(12) United States Patent
Kang

(10) Patent No.: US 10,707,688 B2
(45) Date of Patent: Jul. 7, 2020

(54) METHOD AND APPARATUS FOR HIGH SPEED CHARGING USING VARIOUS CHARGING SCHEMES

(71) Applicant: Samsung Electronics Co., Ltd., Gyeonggi-do (KR)

(72) Inventor: Ba-Da Kang, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 617 days.

(21) Appl. No.: 15/399,930

(22) Filed: Jan. 6, 2017

(65) Prior Publication Data
US 2017/0222459 A1    Aug. 3, 2017

(30) Foreign Application Priority Data
Feb. 3, 2016  (KR) .......................... 10-2016-0013577

(51) Int. Cl.
*H02J 7/00* (2006.01)
*H01R 31/06* (2006.01)

(52) U.S. Cl.
CPC .......... *H02J 7/0045* (2013.01); *H01R 31/065* (2013.01); *H02J 7/007* (2013.01);
(Continued)

(58) Field of Classification Search
CPC .................................................. H02J 7/0045
(Continued)

(56) References Cited

U.S. PATENT DOCUMENTS 6,105,143 A * 8/2000 Kim ..................... G06F 1/266
                                                    713/324
2014/0208134 A1  7/2014 Waters et al.
(Continued)

FOREIGN PATENT DOCUMENTS

KR  10-2010-0029910 A   3/2010
WO     2014/099980 A1   6/2014

OTHER PUBLICATIONS

Choetech, [Type C Charger] CHOE 30W USB 2.0 to Type C Quick Charge 2.0 Adaptive Fast Car Charger for Lumia 950xl/950, Nexus 5x/Nexus 6p, Apple New Macbook 12 Inch A1534, Chromebook Pixel 2 C1501W, pp. 1-2 http://www.amazon.com/gp/product/B01582ELMC/ref=as_li_tl?ie=UTF8&camp=1789&creative=390957&creativeASIN=B01582ELMC&linkCode=as2&tag=androheadl04-20&linkId=TUTM4GJXK6ASA4GB.

*Primary Examiner* — David V Henze-Gongola
(74) *Attorney, Agent, or Firm* — Cha & Reiter, LLC.

(57) ABSTRACT

An electronic device and method are provided. The electronic device includes a first connector including first conductive pins arranged according to a first protocol, a second connector including second conductive pins arranged according to a second protocol and different in number, and a control circuit operatively coupled to the first and second connector. The control circuit detects coupling to an external device through the first connector by at least one of the first conductive pins, receives profile information including at least one of: a power supply device operatively coupled to the second connector and identification information for an external device, and sets a charging path within the electronic device between the first connector and the second connector using at least one of the first conductive pins and the at least one of the second conductive pins coupled to the power supply device.

16 Claims, 19 Drawing Sheets

(52) U.S. Cl.
CPC ............... *H02J 7/0042* (2013.01); *H02J 7/00* (2013.01); *H02J 7/00034* (2020.01)

(58) Field of Classification Search
USPC ........................................................ 320/106
See application file for complete search history.

(56) References Cited

U.S. PATENT DOCUMENTS

| | | |
|---|---|---|
| 2015/0207521 A1 | 7/2015 | Waters |
| 2016/0062935 A1* | 3/2016 | Talmola .................. G06F 1/266 |
| | | 710/306 |
| 2016/0364360 A1* | 12/2016 | Lim ....................... H01R 24/60 |

* cited by examiner

METHOD AND APPARATUS FOR HIGH SPEED CHARGING USING VARIOUS CHARGING SCHEMES

CLAIM OF PRIORITY

This application claims priority under 35 U.S.C. § 119(a) to Korean Application Serial No. 10-2016-0013577, which was filed in the Korean Intellectual Property Office on Feb. 3, 2016, the entire content of which is hereby incorporated by reference.

TECHNICAL FIELD

The present disclosure relates to a method and an apparatus for high speed charging using various charging schemes.

BACKGROUND

With the recent development of digital technologies, various electronic devices including mobile communication terminals, Personal Digital Assistants (PDAs), electronic organizers, smart phones, tablet Personal Computers (PCs), or wearable devices which can perform communication and process personal information while being carried have come to market. The electronic device has various functions such as message transmission like a voice call, a Short Message Service (SMS)/Multimedia Message Service (MMS), a video call, electronic organizer, photography, email transmission/reception, broadcast reproduction, Internet, music reproduction, schedule management, Social Networking Service (SNS), messenger, dictionary, game, and the like.

The electronic device uses a battery for portability. The battery of the electronic device requires charging, and battery charging methods include wired charging and wireless charging. Further, as the use of the battery increases according to improving usability of the electronic device, the electronic device may use a high speed charging function by which the battery can be rapidly charged.

Meanwhile, an interface of a USB 3.1 type C standard (hereinafter, referred to as a "USB type C" interface) has been recently commercialized as an interface by which data can be exchanged through a cable-based wired method. The USB type C interface may have a symmetrical structure and connections between USB interfaces (e.g., USB connectors) of the electronic device may be made through a USB cable regardless of directivity. For example, since connectors at both ends of the USB cable may have the same shape (e.g., form) and the connector does not distinguish between top and bottom, an immediate connection is possible without matching pin directivity of the connectors.

A high speed charger may support various charging schemes such as Adaptive Fast Charging (AFC), Quick Charging (QC), or Power Delivery (PD). A charger using the USB 3.1 type C interface may provide high speed charging through the PD charging scheme. In this case, when a charger uses the AFC or QC charging scheme, the USB 3.1 type C interface does not provide high speed charging.

SUMMARY

Various embodiments may provide a method and an apparatus for providing high speed charging to an electronic device through various charging schemes regardless of a charging scheme of a power supply device or a charging connector type.

In accordance with an aspect of the present disclosure, an electronic device is provided. The electronic device includes a first connector including first conductive pins arranged according to a first protocol, a second connector including second conductive pins arranged according to a second protocol different from the first protocol, the second conductive pins being different in number from the first conductive pins, and a control circuit operatively coupled to the first connector and the second connector. The control circuit is configured to: detect coupling to an external device through the first connector by at least one of the first conductive pins, receive profile information including at least one of: a power supply device operatively coupled to the second connector by at least one of the second conductive pins, and identification information for an external device, and set a charging path within the electronic device between the first connector and the second connector using at least one of the first conductive pins and the at least one of the second conductive pins coupled to the power supply device.

In accordance with another aspect of the present disclosure, a method of operating an electronic device is provided. The method includes detecting an operative coupling of an external device with the electronic device using at least one of first conductive pins arranged according to a first protocol of a first connector, receiving at least one of: profile information indicating a capability of a power supply device operatively coupled through at least one of second conductive pins arranged according to a second protocol of a second connector different from the first protocol, the second conductive pins being different in number from the first conductive pins, and identification for the external device; and setting a charging path between the first connector and the second connector using at least one of the first conductive pins operatively coupled to the external device and the at least one of the second conductive pins operatively coupled to the power supply device.

According to various embodiments, it is possible to provide high speed charging to an electronic device through various charging schemes regardless of a charging scheme of a power supply device.

According to various embodiments, it is possible to provide a current supplied from the power supply device to the electronic device through a first charging path when a charging scheme of the power supply device is the same as a charging scheme of the electronic device, and to provide a current supplied from the power supply device to the electronic device through a second charging path when the charging scheme of the power supply device is different from the charging scheme of the electronic device.

According to various embodiments, even though the charging scheme of the power supply device is different form the charging scheme of the electronic device, it is possible to determine a charging path based on the charging scheme of the power supply device and the charging scheme of the electronic device, so as to conveniently charge the electronic device through the determined charging scheme.

BRIEF DESCRIPTION OF THE DRAWINGS

The above and other aspects and features of the present disclosure will be more apparent from the following detailed description taken in conjunction with the accompanying drawings, in which.

DETAILED DESCRIPTION

Figure 1:
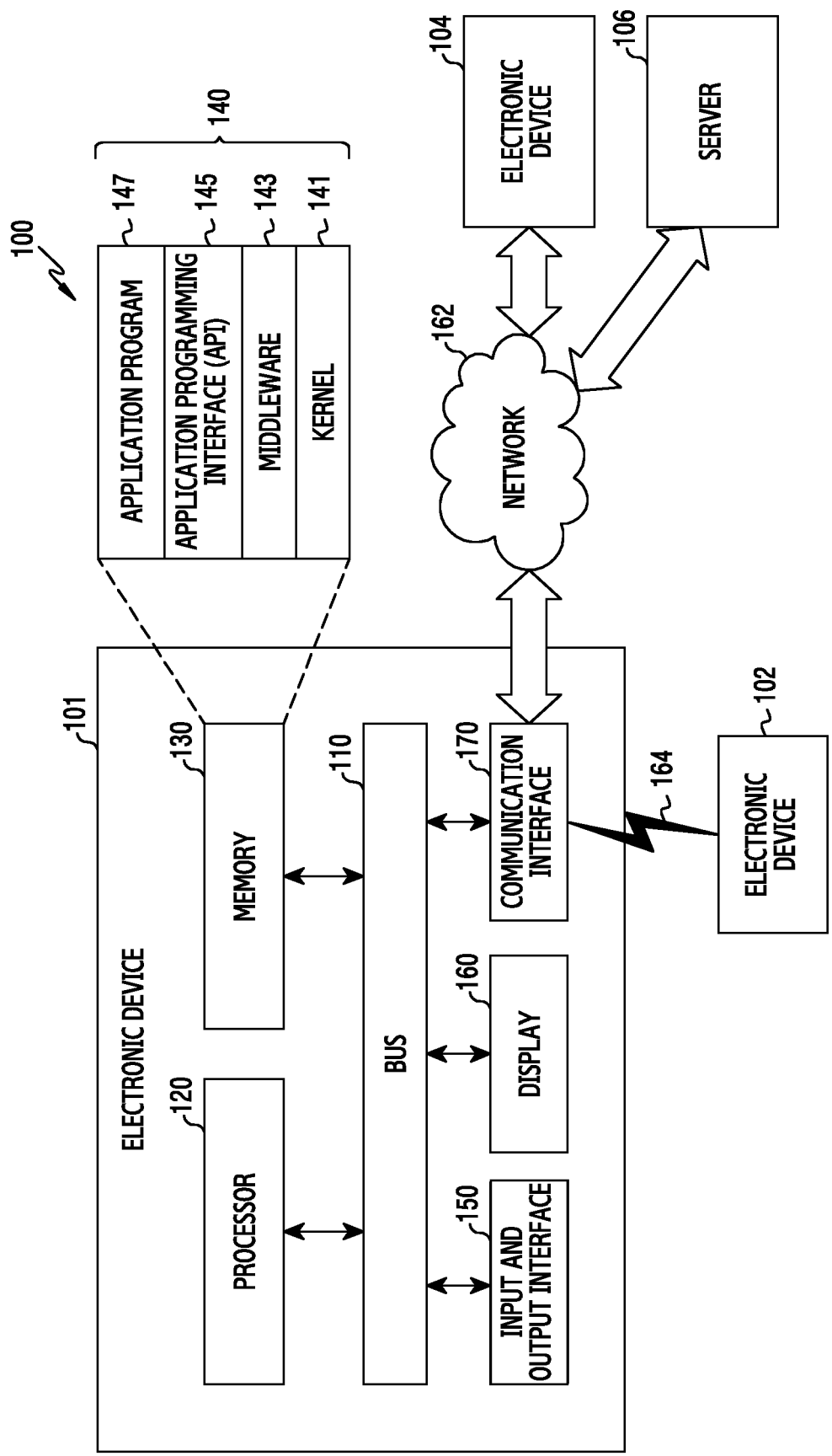
FIG. 1 is a diagram illustrating an electronic device within a network environment according to various embodiments.

Hereinafter, various embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements.

As used herein, the expression "have", "may have", "include", or "may include" refers to the existence of a corresponding feature (e.g., numeral, function, operation, or constituent element such as component), and does not exclude one or more additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B. The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit).

According to some embodiments, the electronic device may be a home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device according to various embodiments of the present disclosure may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology.

Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 illustrates a network environment including an electronic device according to various embodiments of the present disclosure.

An electronic device 101 within a network environment 100, according to various embodiments, will be described with reference to FIG. 1. The electronic device 101 may include a bus 110, a processor 120, a memory 130, an input/output interface 150, a display 160, and a communication interface 170. According to an embodiment of the present disclosure, the electronic device 101 may omit at least one of the above components or may further include other components.

The bus 110 may include, for example, a circuit which interconnects the components 110 to 170 and delivers a communication (e.g., a control message and/or data) between the components 110 to 170.

The processor 120 may include one or more of a Central Processing Unit (CPU), an Application Processor (AP), and a Communication Processor (CP). The processor 120 may carry out, for example, calculation or data processing relating to control and/or communication of at least one other component of the electronic device 101.

The memory 130 may include a volatile memory and/or a non-volatile memory. The memory 130 may store, for example, commands or data relevant to at least one other component of the electronic device 101. According to an embodiment of the present disclosure, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an Operating System (OS).

The kernel 141 may control or manage system resources (e.g., the bus 110, the processor 120, or the memory 130) used for performing an operation or function implemented in the other programs (e.g., the middleware 143, the API 145, or the application programs 147). Furthermore, the kernel 141 may provide an interface through which the middleware 143, the API 145, or the application programs 147 may access the individual components of the electronic device 101 to control or manage the system resources.

The middleware 143, for example, may serve as an intermediary for allowing the API 145 or the application programs 147 to communicate with the kernel 141 to exchange data.

Also, the middleware 143 may process one or more task requests received from the application programs 147 according to priorities thereof. For example, the middleware 143 may assign priorities for using the system resources (e.g., the bus 110, the processor 120, the memory 130, or the like) of the electronic device 101, to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (e.g., instruction) for file control, window control, image processing, character control, and the like.

The input/output interface 150, for example, may function as an interface that may transfer commands or data input from a user or another external device to the other element(s) of the electronic device 101. Furthermore, the input/output interface 150 may output the commands or data received from the other element(s) of the electronic device 101 to the user or another external device.

Examples of the display 160 may include a Liquid Crystal Display (LCD), a Light-Emitting Diode (LED) display, an Organic Light-Emitting Diode (OLED) display, a MicroElectroMechanical Systems (MEMS) display, and an electronic paper display. The display 160 may display, for example, various types of contents (e.g., text, images, videos, icons, or symbols) to users. The display 160 may include a touch screen, and may receive, for example, a touch, gesture, proximity, or hovering input using an electronic pen or a user's body part.

The communication interface 170 may establish communication, for example, between the electronic device 101 and an external device (e.g., a first external electronic device 102, a second external electronic device 104, or a server 106). For example, the communication interface 170 may be connected to a network 162 through wireless or wired communication, and may communicate with an external device (e.g., the second external electronic device 104 or the server 106). The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. In addition, the wireless communication may include, for example, short range communication 164. The short range communication 164 may include at least one of, for example, Wi-Fi, Bluetooth, Near Field Communication (NFC), and Global Navigation Satellite System (GNSS). GNSS may include, for example, at least one of global positioning system (GPS), global navigation satellite system (Glonass), Beidou Navigation satellite system (Beidou) or Galileo, and the European global satellite-based navigation system, based on a location, a bandwidth, or the like. Hereinafter, in the present disclosure, the "GPS" may be interchangeably used with the "GNSS". The wired communication may include, for example, at least one of a Universal Serial Bus (USB), a High Definition Multimedia Interface (HDMI), Recommended Standard 232 (RS-232), and a Plain Old Telephone Service (POTS). The network 162 may include at least one of a telecommunication network such as a computer network (e.g., a LAN or a WAN), the Internet, and a telephone network.

Each of the first and second external electronic devices 102 and 104 may be of a type identical to or different from that of the electronic device 101. According to an embodiment of the present disclosure, the server 106 may include a group of one or more servers. According to various embodiments of the present disclosure, all or some of the operations performed in the electronic device 101 may be executed in another electronic device or a plurality of electronic devices (e.g., the electronic devices 102 and 104 or the server 106). According to an embodiment of the present disclosure, when the electronic device 101 has to perform some functions or services automatically or in response to a request, the electronic device 101 may request another device (e.g., the electronic device 102 or 104 or the server 106) to execute at least some functions relating thereto instead of or in addition to autonomously performing the functions or services. Another electronic device (e.g., the electronic device 102 or 104, or the server 106) may execute the requested functions or the additional functions, and may deliver a result of the execution to the electronic device 101. The electronic device 101 may process the received result as it is or additionally, and may provide the requested functions or services. To this end, for example, cloud computing, distributed computing, or client-server computing technologies may be used.

Figure 2:
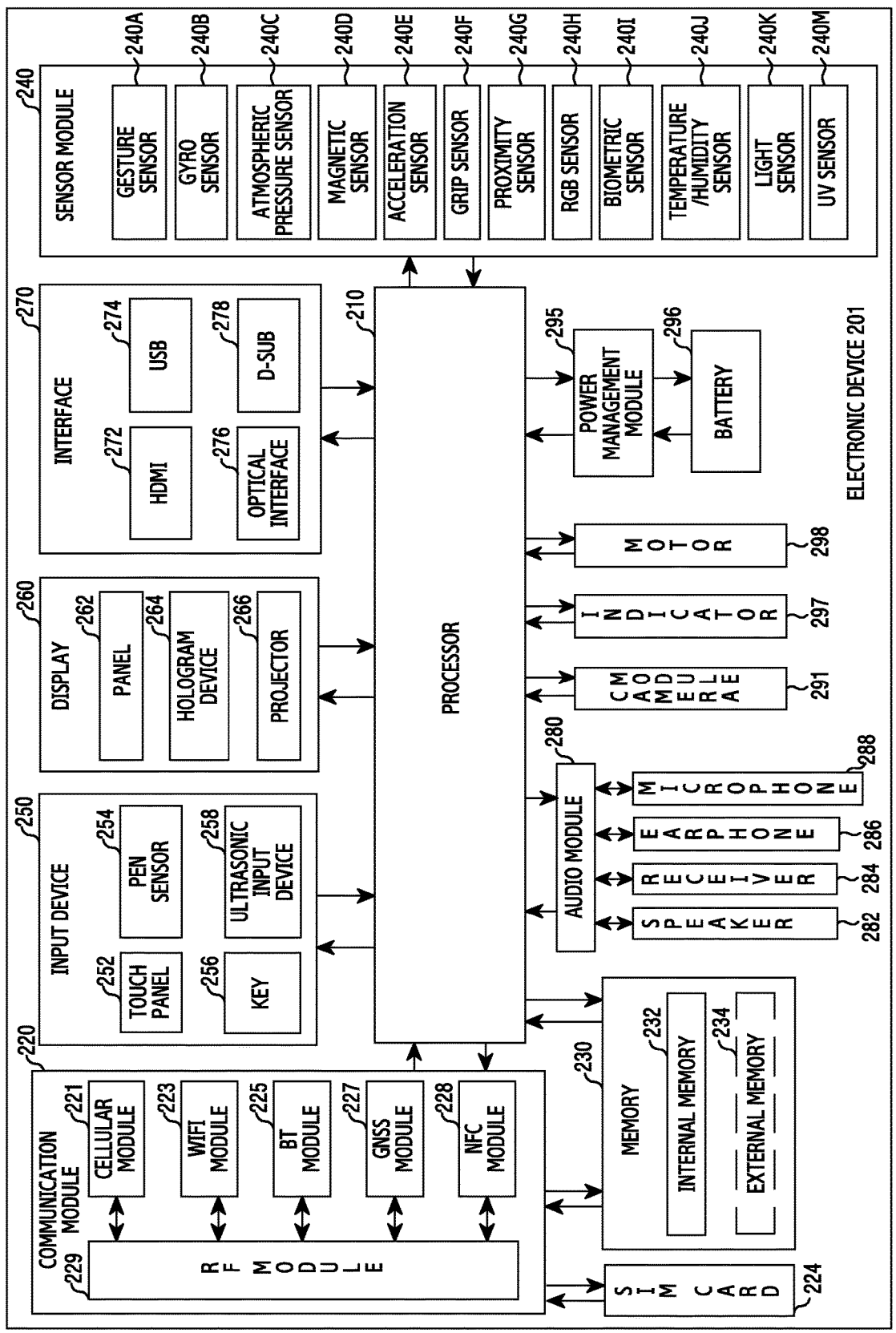
FIG. 2 is a block diagram illustrating a configuration of the electronic device according to various embodiments.

FIG. 2 is a block diagram of an electronic device according to various embodiments of the present disclosure.

The electronic device 201 may include, for example, all or a part of the electronic device 101 shown in FIG. 1. The electronic device 201 may include one or more processors 210 (e.g., Application Processors (AP)), a communication module 220, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program, and perform processing of various pieces of data and calculations. The processor 210 may be embodied as, for example, a System on Chip (SoC). According to an embodiment of the present disclosure, the processor 210 may further include a Graphic Processing Unit (GPU) and/or an image signal processor. The processor 210 may include at least some (e.g., a cellular module 221) of the components illustrated in FIG. 2. The processor 210 may load, into a volatile memory, commands or data received from at least one (e.g., a non-volatile memory) of the other components and may process the loaded commands or data, and may store various data in a non-volatile memory.

The communication module 220 may have a configuration equal or similar to that of the communication interface 170 of FIG. 1. The communication module 220 may include, for example, a cellular module 221, a Wi-Fi module 223, a BT module 225, a GNSS module 227 (e.g., a GPS module 227, a Glonass module, a Beidou module, or a Galileo module), an NFC module 228, and a Radio Frequency (RF) module 229.

The cellular module 221, for example, may provide a voice call, a video call, a text message service, or an Internet service through a communication network. According to an embodiment of the present disclosure, the cellular module 221 may distinguish and authenticate the electronic device 201 in a communication network using a subscriber identification module (e.g., SIM card) 224 (e.g., the SIM card). According to an embodiment of the present disclosure, the cellular module 221 may perform at least some of the functions that the processor 210 may provide. According to an embodiment of the present disclosure, the cellular module 221 may include a communication processor (CP).

For example, each of the Wi-Fi module 223, the BT module 225, the GNSS module 227, and the NFC module 228 may include a processor for processing data transmitted/received through a corresponding module. According to an embodiment of the present disclosure, at least some (e.g., two or more) of the cellular module 221, the Wi-Fi module 223, the BT module 225, the GNSS module 227, and the NFC module 228 may be included in one Integrated Chip (IC) or IC package.

The RF module 229, for example, may transmit/receive a communication signal (e.g., an RF signal). The RF module 229 may include, for example, a transceiver, a Power Amplifier Module (PAM), a frequency filter, a Low Noise Amplifier (LNA), and an antenna. According to another embodiment of the present disclosure, at least one of the cellular module 221, the Wi-Fi module 223, the BT module 225, the GNSS module 227, and the NFC module 228 may transmit/receive an RF signal through a separate RF module.

The subscriber identification module 224 may include, for example, a card including a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (e.g., the memory 130) may include, for example, an embedded memory 232 or an external memory 234. The embedded memory 232 may include at least one of a volatile memory (e.g., a Dynamic Random Access Memory (DRAM), a Static RAM (SRAM), a Synchronous Dynamic RAM (SDRAM), and the like) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (e.g., a NAND flash memory or a NOR flash memory), a hard disc drive, a Solid State Drive (SSD), and the like).

The external memory 234 may further include a flash drive, for example, a Compact Flash (CF), a Secure Digital (SD), a Micro Secure Digital (Micro-SD), a Mini Secure Digital (Mini-SD), an eXtreme Digital (xD), a MultiMediaCard (MMC), a memory stick, or the like. The external memory 234 may be functionally and/or physically connected to the electronic device 201 through various interfaces.

The sensor module 240, for example, may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor (barometer) 240C, a magnetic sensor 240D, an acceleration sensor 240E, a grip sensor 240F, a proximity sensor 240G, a color sensor 240H (e.g., red, green, and blue (RGB) sensor), a biometric sensor (medical sensor) 240I, a temperature/humidity sensor 240J, an illuminance sensor 240K, and a Ultra Violet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris scan sensor, and/or a finger scan sensor. The sensor module 240 may further include a control circuit for controlling one or more sensors included therein. According to an embodiment of the present disclosure, the electronic device 201 may further include a processor configured to control the sensor module 240, as a part of the processor 210 or separately from the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer, and provide a tactile reaction to the user.

The (digital) pen sensor 254 may include, for example, a recognition sheet which is a part of the touch panel or is separated from the touch panel. The key 256 may include, for example, a physical button, an optical key or a keypad. The ultrasonic input device 258 may detect, through a microphone (e.g., the microphone 288), ultrasonic waves generated by an input tool, and identify data corresponding to the detected ultrasonic waves.

The display 260 (e.g., the display 160) may include a panel 262, a hologram device 264, or a projector 266. The panel 262 may include a configuration identical or similar to the display 160 illustrated in FIG. 1. The panel 262 may be implemented to be, for example, flexible, transparent, or wearable. The panel 262 may be embodied as a single module with the touch panel 252. The hologram device 264 may show a three dimensional (3D) image in the air by using an interference of light. The projector 266 may project light onto a screen to display an image. The screen may be located, for example, in the interior of or on the exterior of the electronic device 201. According to an embodiment of the present disclosure, the display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-sub-miniature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280, for example, may bilaterally convert a sound and an electrical signal. At least some components of the audio module 280 may be included in, for example, the input/output interface 150 illustrated in FIG. 1. The audio module 280 may process voice information input or output through, for example, a speaker 282, a receiver 284, earphones 286, or the microphone 288.

The camera module 291 is, for example, a device which may photograph a still image and a video. According to an embodiment of the present disclosure, the camera module 291 may include one or more image sensors (e.g., a front sensor or a back sensor), a lens, an Image Signal Processor (ISP) or a flash (e.g., LED or xenon lamp).

The power management module 295 may manage, for example, power of the electronic device 201. According to an embodiment of the present disclosure, the power management module 295 may include a Power Management Integrated Circuit (PMIC), a charger Integrated Circuit (IC), or a battery or fuel gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual quantity of the battery 296, and a voltage, a current, or a temperature while charging. The battery 296 may include, for example, a rechargeable battery and/or a solar battery.

The indicator 297 may display a particular state (e.g., a booting state, a message state, a charging state, or the like) of the electronic device 201 or a part (e.g., the processor 210) of the electronic device 201. The motor 298 may convert an electrical signal into a mechanical vibration, and may generate a vibration, a haptic effect, or the like. Although not illustrated, the electronic device 201 may include a processing device (e.g., a GPU) for supporting a mobile TV. The processing device for supporting a mobile TV may process, for example, media data according to a certain standard such as Digital Multimedia Broadcasting (DMB), Digital Video Broadcasting (DVB), or media-FLO™.

Each of the above-described component elements of hardware according to the present disclosure may be configured with one or more components, and the names of the corresponding component elements may vary based on the type of electronic device. In various embodiments, the electronic device may include at least one of the above-described elements. Some of the above-described elements may be omitted from the electronic device, or the electronic device may further include additional elements. Also, some of the hardware components according to various embodiments may be combined into one entity, which may perform functions identical to those of the relevant components before the combination.

Figure 3:
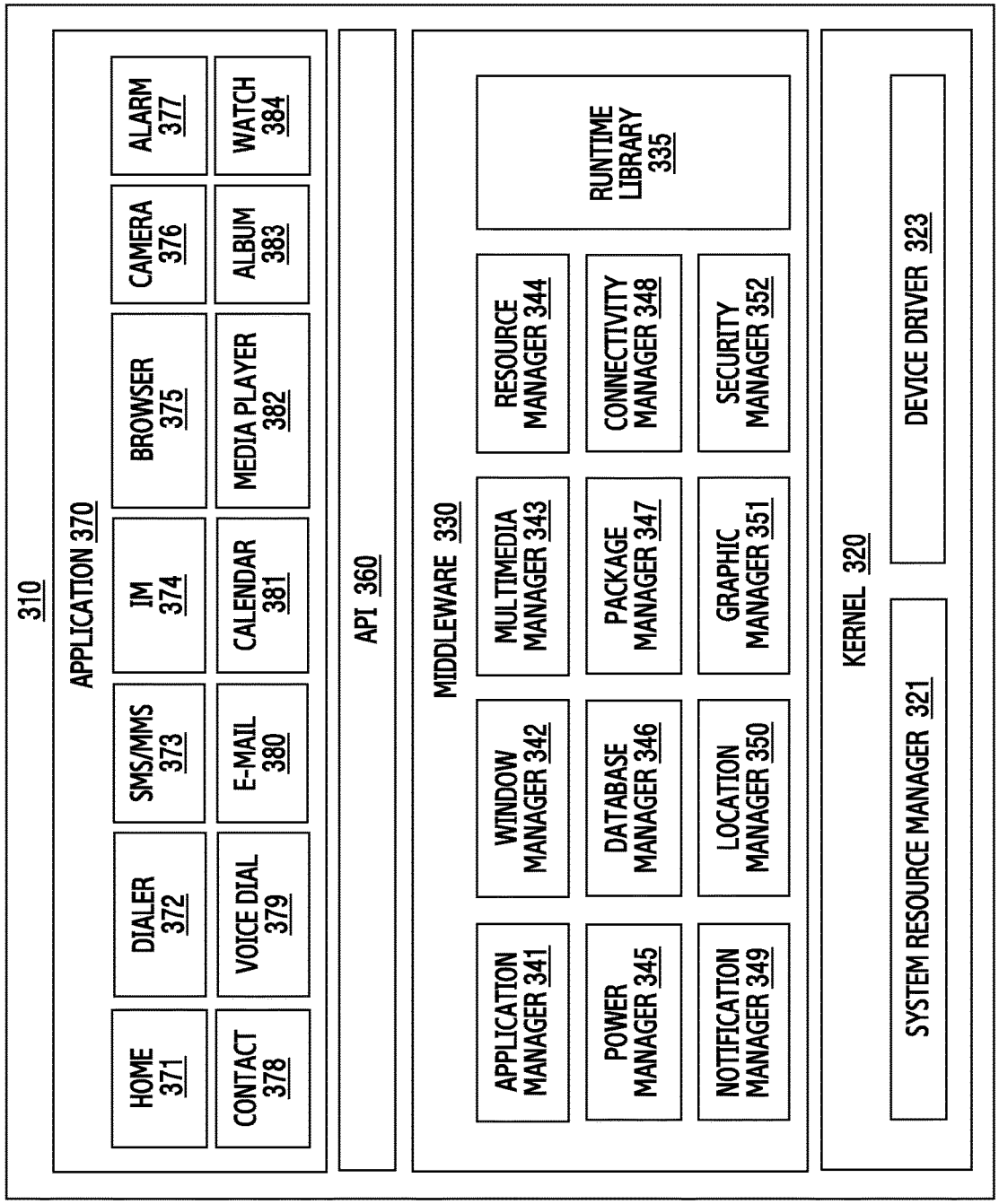
FIG. 3 is a block diagram of a program module according to various embodiments.

FIG. 3 is a block diagram of a program module according to various embodiments of the present disclosure.

According to an embodiment of the present disclosure, the program module 310 (e.g., the program 140) may include an Operating System (OS) for controlling resources related to the electronic device (e.g., the electronic device 101) and/or various applications (e.g., the application programs 147) executed in the operating system. The operating system may be, for example, Android™, iOS™, Windows™, Symbian™, Tizen™, Bada™, or the like.

The program module 310 may include a kernel 320, middleware 330, an API 360, and/or applications 370. At least some of the program module 310 may be preloaded on an electronic device, or may be downloaded from an external electronic device (e.g., the electronic device 102 or 104, or the server 106).

The kernel 320 (e.g., the kernel 141) may include, for example, a system resource manager 321 and/or a device driver 323. The system resource manager 321 may control, allocate, or collect system resources. According to an embodiment of the present disclosure, the system resource manager 321 may include a process management unit, a memory management unit, a file system management unit, and the like. The device driver 323 may include, for example, a display driver, a camera driver, a Bluetooth driver, a shared memory driver, a USB driver, a keypad driver, a Wi-Fi driver, an audio driver, or an Inter-Process Communication (IPC) driver.

For example, the middleware 330 may provide a function utilized in common by the applications 370, or may provide various functions to the applications 370 through the API 360 so as to enable the applications 370 to efficiently use the limited system resources in the electronic device. According to an embodiment of the present disclosure, the middleware 330 (e.g., the middleware 143) may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while an application 370 is being executed. The runtime library 335 may perform input/output management, memory management, the functionality for an arithmetic function, or the like.

The application manager 341 may manage, for example, a life cycle of at least one of the applications 370. The window manager 342 may manage Graphical User Interface (GUI) resources used by a screen. The multimedia manager 343 may recognize a format utilized for reproduction of various media files, and may perform encoding or decoding of a media file by using a codec suitable for the corresponding format. The resource manager 344 may manage resources of a source code, a memory, and a storage space of at least one of the applications 370.

The power manager 345 may operate together with, for example, a Basic Input/Output System (BIOS) or the like to manage a battery or power source and may provide power information or the like utilized for the operations of the electronic device. The database manager 346 may generate, search for, and/or change a database to be used by at least one of the applications 370. The package manager 347 may manage installation or an update of an application distributed in a form of a package file.

For example, the connectivity manager 348 may manage wireless connectivity such as Wi-Fi or Bluetooth. The notification manager 349 may display or notify of an event such as an arrival message, promise, proximity notification, and the like in such a way that does not disturb a user. The location manager 350 may manage location information of an electronic device. The graphic manager 351 may manage a graphic effect which will be provided to a user, or a user interface related to the graphic effect. The security manager 352 may provide all security functions utilized for system security, user authentication, or the like. According to an embodiment of the present disclosure, when the electronic device (e.g., the electronic device 101) has a telephone call function, the middleware 330 may further include a telephony manager for managing a voice call function or a video call function of the electronic device.

The middleware 330 may include a middleware module that forms a combination of various functions of the above-described components. The middleware 330 may provide a module specialized for each type of OS in order to provide a differentiated function. Further, the middleware 330 may dynamically remove some of the existing components or add new components.

The API 360 (e.g., the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 (e.g., the application programs 147) may include, for example, one or more applications which may provide functions such as a home 371, a dialer 372, an SMS/MMS 373, an Instant Message (IM) 374, a browser 375, a camera 376, an alarm 377, contacts 378, a voice dial 379, an email 380, a calendar 381, a media player 382, an album 383, a clock or watch 384, in addition to any other desirable program, such as a health care program (e.g., for measuring exercise quantity or blood sugar), or environment information program (e.g., for providing atmospheric pressure, humidity, or temperature information).

According to an embodiment of the present disclosure, the applications 370 may include an application (hereinafter, referred to as an "information exchange application" for convenience of description) that supports exchanging information between the electronic device (e.g., the electronic device 101) and an external electronic device (e.g., the electronic device 102 or 104). The information exchange application may include, for example, a notification relay application for transferring specific information to an external electronic device or a device management application for managing an external electronic device.

For example, the notification relay application may include a function of transferring, to the external electronic device (e.g., the electronic device 102 or 104), notification information generated from other applications of the electronic device 101 (e.g., an SMS/MMS application, an e-mail application, a health management application, or an environmental information application). Further, the notification relay application may receive notification information from, for example, an external electronic device and provide the received notification information to a user.

The device management application may manage (e.g., install, delete, or update), for example, at least one function of an external electronic device (e.g., the electronic device 102 or 104) communicating with the electronic device (e.g., a function of turning on/off the external electronic device itself (or some components) or a function of adjusting the brightness (or a resolution) of the display), applications operating in the external electronic device, and services provided by the external electronic device (e.g., a call service or a message service).

According to an embodiment of the present disclosure, the applications 370 may include applications (e.g., a health care application of a mobile medical appliance or the like) designated according to an external electronic device (e.g., attributes of the electronic device 102 or 104). According to an embodiment of the present disclosure, the applications 370 may include an application received from an external electronic device (e.g., the server 106, or the electronic device 102 or 104). According to an embodiment of the present disclosure, the applications 370 may include a preloaded application or a third party application that may be downloaded from a server. The names of the components of the program module 310 of the illustrated embodiment of the present disclosure may change according to the type of operating system.

According to various embodiments, at least a part of the programming module 310 may be implemented in software, firmware, hardware, or a combination of two or more thereof. At least some of the program module 310 may be implemented (e.g., executed) by, for example, the processor (e.g., the processor 210). At least some of the program module 310 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter.

According to various embodiments, at least some of the devices (e.g., modules or functions thereof) or the method (e.g., operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable recoding media may be, for example, the memory 130.

Figure 4:
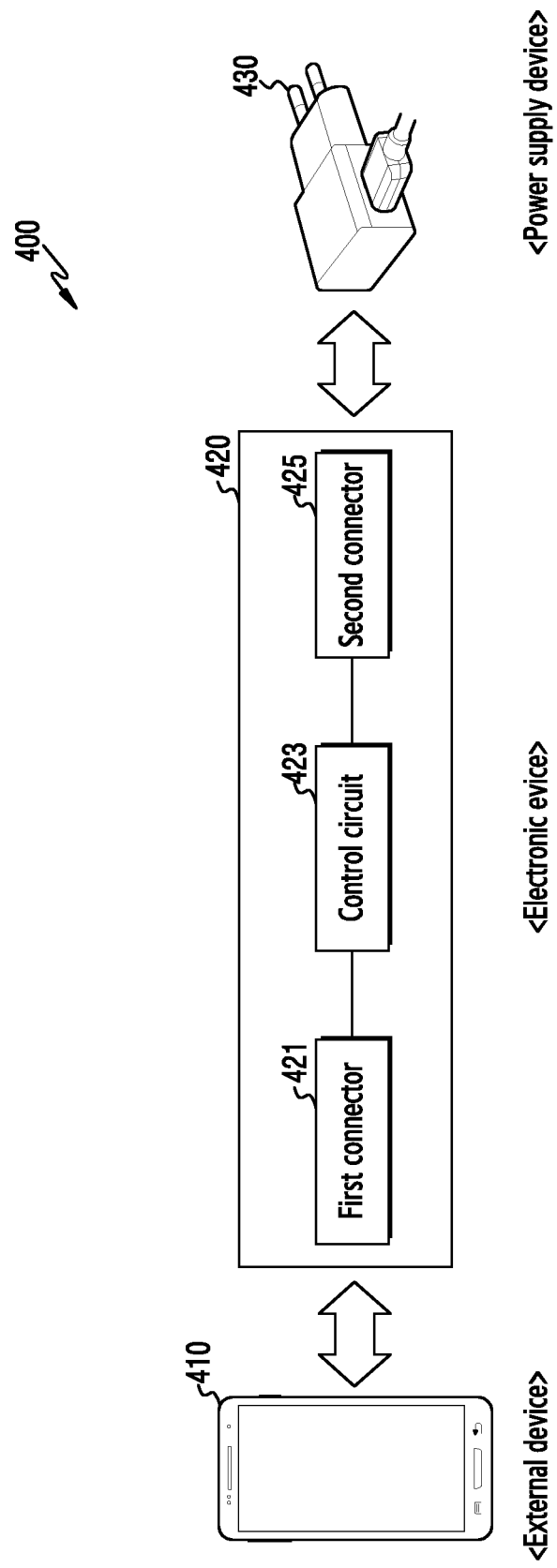
FIG. 4 illustrates a connection relationship between an electronic device and external devices according to various embodiments.

FIG. 4 illustrates a connection relationship between an electronic device and external devices according to various embodiments.

Referring to FIG. 4, an example in which an external device 410 and a power supply device 430 are connected to an electronic device 420 in a connection relationship 400 is illustrated. Hereinafter, devices except for the electronic device 420 may be described as "external" devices. For example, in FIG. 4, the external device 410 and the power supply device 430 may correspond to the "external" devices.

The external device 410 according to an embodiment of the present disclosure may be the electronic device 101 of FIG. 1 or the electronic device 201 of FIG. 2. When the external device 410 is connected to the electronic device 420, the external device 410 may receive power from the power supply device 430 connected to the electronic device 420. That is, the external device 410 may be a portable terminal having a battery embedded therein (or removable therefrom) like a mobile phone, a smart phone, or a notebook. The external device 410 may be fast charged through the Power Delivery (PD) charging scheme.

The power supply device 430 according to an embodiment of the present disclosure may be a travel adapter and may support high speed charging or normal charging. The power supply device 430 may provide power through various protocols. For example, the power supply device 430 may supply power through one of the AFC, QC, and PD charging schemes. The voltage or current for the fast charging or the voltage or current for the normal charging may vary depending on the charging scheme.

The electronic device 420 according to an embodiment of the present disclosure may include a first connector 421 (or a first electrical interface), a second connector 425 (or a second electrical interface), and a control circuit 423.

As the first connector 421, a Universal Serial Bus (USB) type C interface (or connector) may be adopted. The USB type C interface supports a USB 3.1 protocol and the USB 3.1 protocol corresponds to a protocol which can provide a maximum of 100 W power with a maximum of 20 V and 5 A. Accordingly, when the USB type C interface is adapted, the high speed charging may be facilitated. The first connector 421 may be electrically connected to the external device 410. For example, when the external device 410 is connected, the first connector 421 may detect a signal from at least one of a VBUS pin, a "Configuration Channel" or CC1 pin, and similarly a CC2 pin. The first connector 421 may include CC1 and CC2 for coupling direction recognition and digital data communication and their roles may be defined as a host device (e.g., a Downstream Facing Port: DFP) and a slave device (e.g., an Upstream Facing Port: UFP) by pull-up (Rp) or a current source and pull-down (Rd). In the USB type C interface, the side having pull-down (Rd) may be defined as the slave device, and the host device may supply power through a power supply pin (e.g., VBUS or VCONN (e.g., CC1 or CC2)) according to the need of the slave device. Here, the external device 410 connected to the first connector 421 receives power supply, and thus may receive power from the power supply device 430 through the power supply pin.

As the second connector 425, a type of interface that supports a USB 2.0 specification or higher may be adopted. For example, the type that supports the USB 2.0 specification or higher may be of various types such as type B and type C. Further, a protocol supporting the USB 2.0 specification or higher may be at least one of a USB 2.0 protocol, a USB 3.0 protocol and a USB 3.1 protocol. The second connector 425 may have a different number of conductive pins formed therein according to the USB specification or type. The second connector 425 may be electrically connected to the power supply device 430. For example, when the charging scheme of the power supply device 430 is "PD," the second connector 425 may detect a signal from at least one of a VBUS pin, a CC1 pin, and a CC2 pin. Alternatively, when the charging scheme of the power supply device 430 is "AFC" or "QC," the second connector 425 may detect a signal from at least one of the VBUS pin, a D+ pin, and a D− pin.

Similar to the first connector 421, when the second connector 425 is the USB type C interface, the second connector 425 according to an embodiment of the present disclosure may be connected to the power supply device 430 of the "PD" charging scheme. Alternatively, different from the first connector 421, when the second connector 425 is the USB type B interface, the second connector 425 may be connected to the power supply device 430 of the "AFC" or "QC" charging scheme. This is a simple design change, and the USB specification or type of the second connector 425 may be differently formed.

The control circuit 423 may be a processor, for example, a Micro Controller Unit (MCU). The control circuit 423 may detect whether a device is connected to the first connector 421 and the second connector 425 and form a plurality of electrically conductive paths between the first connector 421 and the second connector 425.

When a signal is detected through a CC1 line or a CC2 line of the second connector 425, the control circuit 423 according to an embodiment of the present disclosure may determine that the charging scheme of the power supply device 430 corresponds to "PD." When a signal is detected through a D+ line or and a D− line of the second connector 425, the control circuit 423 may determine that the charging scheme of the power supply device 430 corresponds to "AFC" or "QC".

The control circuit 423 according to an embodiment of the present disclosure may determine a charging path based on the charging scheme of the external device 410 and the charging scheme of the power supply device 430. The protocol transferring a signal may vary depending on the charging scheme. For example, in the PD charging scheme, the control circuit 423 may use a protocol (e.g., USB 3.1 protocol) through the CC line (e.g., CC1 pin or CC2 pin). Further, in the AFC or QC charging scheme, the control circuit 423 may use the protocol (e.g., USB 2.0 protocol) through the D+/D− line. When information exchange between devices is needed, the protocol may refer to a communication protocol for communication between the devices. Accordingly, different charging schemes mean different protocols, so that the electrically conductive path between the first connector 421 and the second connector 425 may be formed to be different from that when the protocols are the same.

For example, when the charging scheme of the external device 410 is the same as the charging scheme of the power supply device 430, the charging path between the external device 410 and the power supply device 430 may be set as a "first charging path." For example, the first charging path means that the electrically conductive path is formed between the CC1 line or the CC2 line of the first connector 421 and the CC1 line or the CC2 line of the second connector 425. When the charging scheme of the external device 410 is different from the charging scheme of the power supply device 430, the control circuit 423 according to an embodiment of the present disclosure may set the charging path between the external device 410 and the power supply device 430 as a "second charging path." For example, the second charging path means that the electrically conductive path is formed between the CC1 line or the CC2 line of the first connector 421 and the D+ line and D− line of the second connector 425.

Figure 5A:
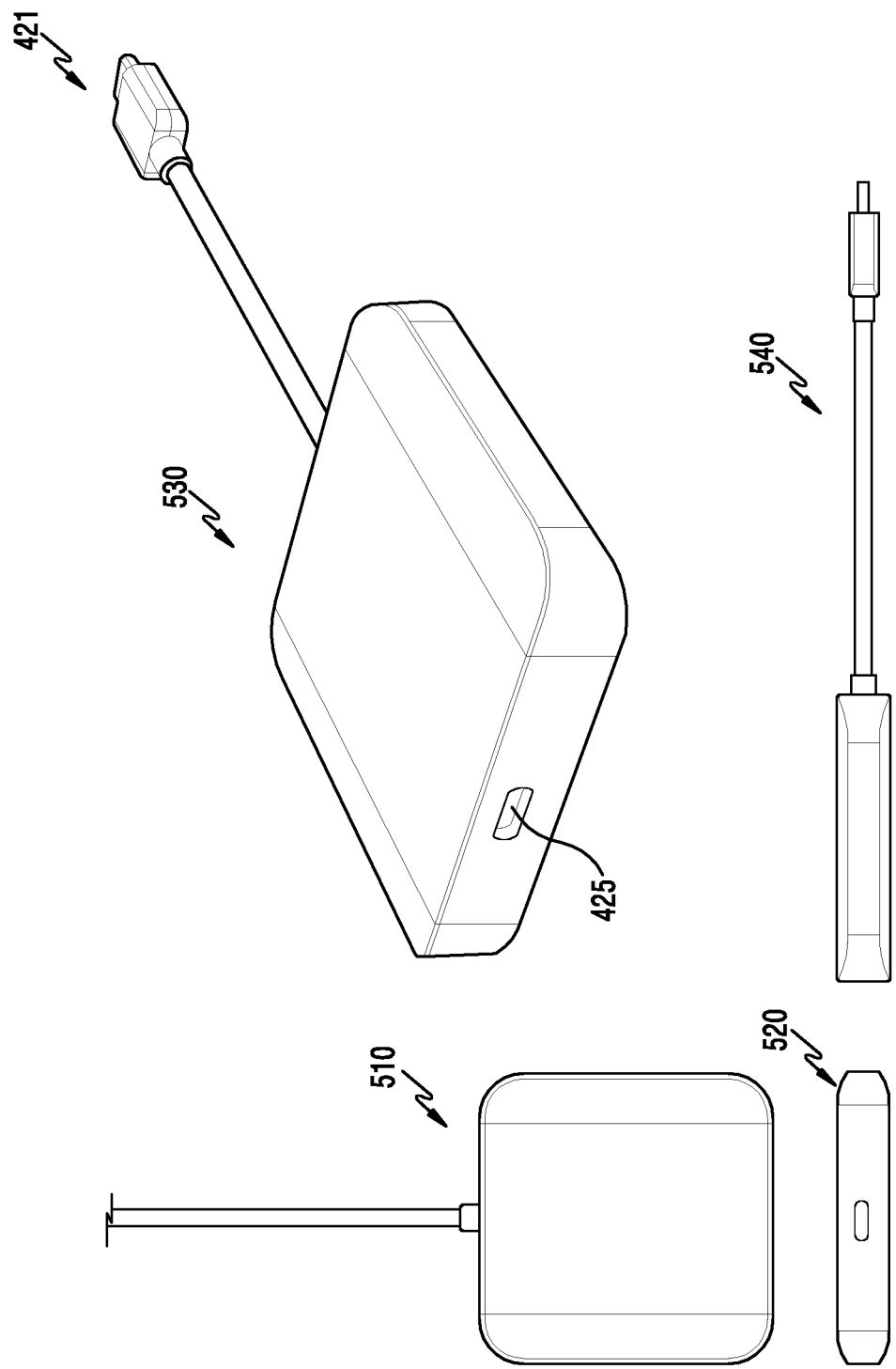
FIG. 5A, FIG. 5B and FIG. 5C are external configuration diagrams and internal circuit diagrams of the electronic device according to various embodiments.
Figure 5B:
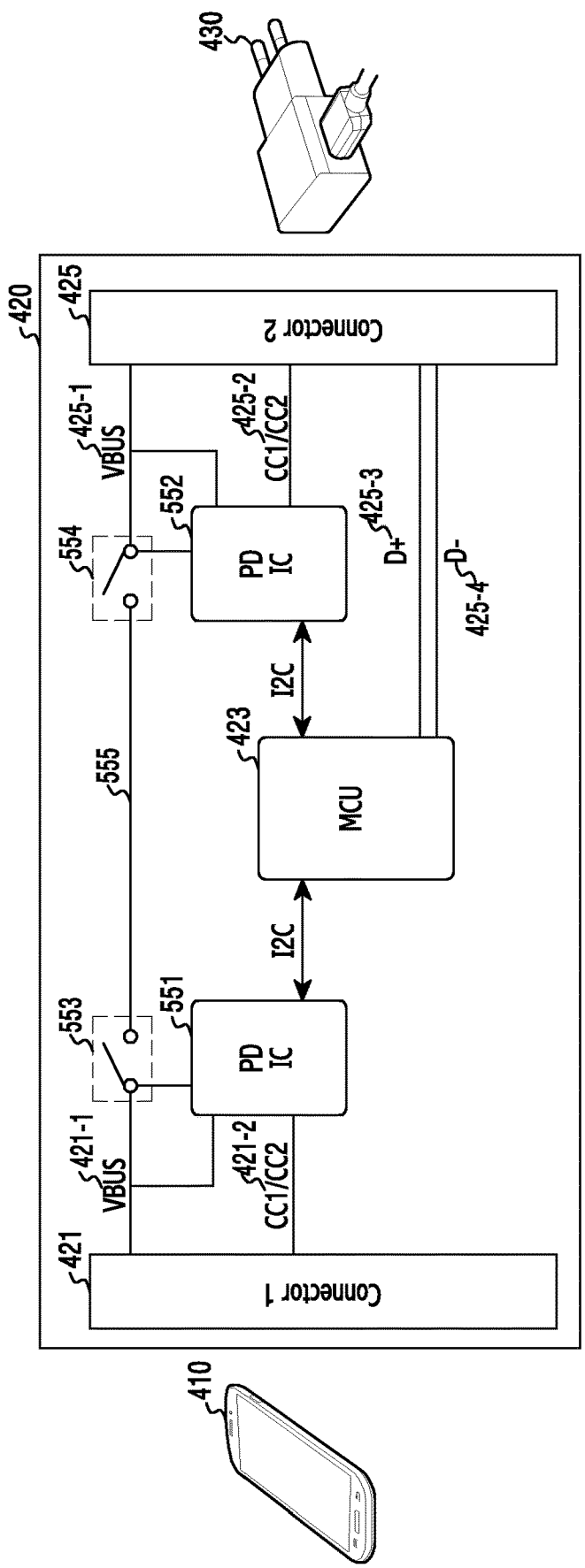
Figure 5C:
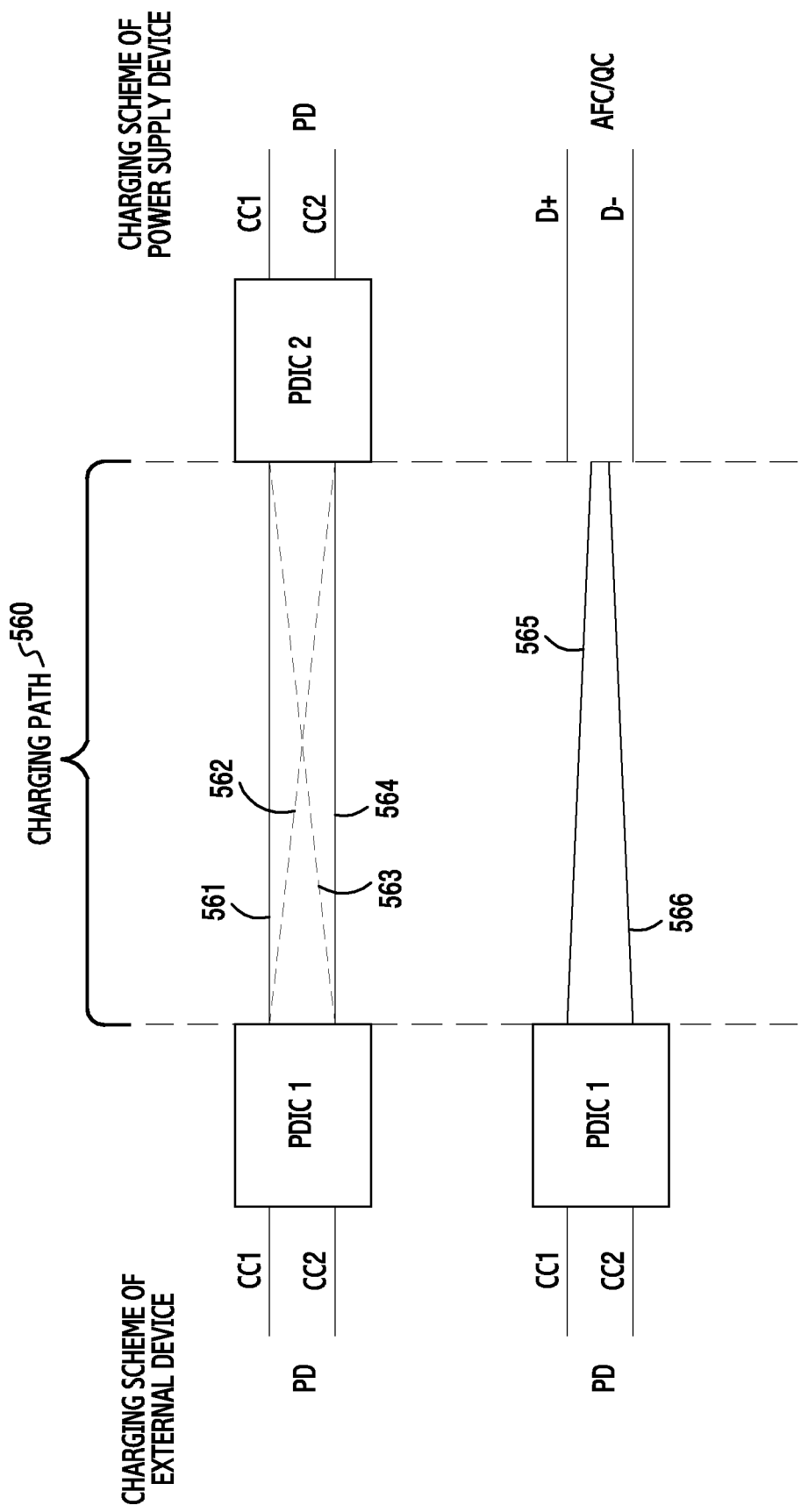

FIGS. 5A to 5C are external configuration diagrams and internal circuit diagrams of the electronic device according to various embodiments.

FIG. 5A is an external configuration diagram of the electronic device 420.

Referring to FIG. 5A, examples of a front view 510 of the electronic device 420, a first side view 520 of the electronic device 420, a perspective view 530 of the electronic device 420, and a second side view 540 of the electronic device 420 are illustrated. The front view 510 of the electronic device 420 is viewed from the top while the electronic device 420 is disposed on the bottom of the perspective view. The first side view 520 of the electronic device 420 shows a portion where the second connector 425 of the electronic device 420 is formed and disposed, when the electronic device 420 is viewed from the front perspective. The second side view 540 of the electronic device 420 shows a portion where neither the first connector 421 nor the second connector 425 of the electronic device 420 are formed or disposed.

The perspective view 530 of the electronic device 420, according to an embodiment of the present disclosure, represents an isometric view of the electronic device 420, allowing visibly of a portion where the second connector 425 of the electronic device 420 is formed and disposed. Referring to the isometric perspective view 530, the electronic device 420 may include a housing (or body), the control circuit 423 disposed within the housing, the first connector 421, and the second connector 425. The first connector 421 may be connected to the housing through a cable having a predetermined length. For example, the first connector 421 may be a male connector, and the second connector 425 may be a female connector. That is, although the first connector 421 and the second connector 425 are illustrated in different forms (e.g., female connector and male connector) in the perspective view 530, the first connector 421 and the second connector 425 may be implemented in the same form (e.g., female connector/female connector or male connector/male connector) according to a design of the electronic device 420 or the female connector and the male connector illustrated in the perspective view 530 may be inversely implemented. For example, the first connector 421 may include a first number of conductive pins arranged according to the first protocol (e.g., USB 3.1). The second connector 425 may include a second number of conductive pins arranged according to the second protocol (e.g., USB 2.0) different from the first protocol, the second number being different from the first number.

Hereinafter, an example of using an MCU as an example of the control circuit 423 will be illustrated. That is, the MCU and the control circuit refer to the same element and use the same reference numeral.

FIG. 5B is a schematic internal circuit diagram of the electronic device 420.

Referring to FIG. 5B, the electronic device 420 may include the first connector (e.g., "connector 1") 421, the second connector (e.g., "connector 2") 425, the MCU 423, a first Power Delivery Integrated Circuit (or "first PDIC") 551, and a second PDIC 552. Communication between chips such as the MCU 423, the first PDIC 551, and the second PDIC 552 may be Inter Integrated Circuit (I2C) communication.

The first connector 421 according to an embodiment of the present disclosure may be a USB 3.1 type C connector. For example, the first connector 421 may include the first number of conductive pins arranged according to the first protocol. The second connector 425 may include the second number of conductive pins arranged according to the second protocol different from the first protocol, the second number being different from the first number. The first connector 421 and the second connector 425 may have the same protocol and the same number of arranged conductive pins. Alternatively, the first connector 421 and the second connector 425 may have different protocols and the different numbers of arranged conductive pins. The first connector 421 and the second connector 425 according to an embodiment of the present disclosure may be different types of connectors.

Although it is illustrated that the first PDIC 551 and the second PDIC 552 are separated from the MCU 423 in FIG. 5B, at least one of the first PDIC 551 and the second PDIC 552 may be included in the MCU 423.

When the external device 410 is connected to the first connector 421 according to an embodiment of the present disclosure, the first PDIC 551 may detect a signal through a VBUS line 421-1 or a CC1/CC2 line 425-2 of the first connector 421. The CC1/CC2 line 421-2 may be connected to an upper part or a lower part of the USB type C interface, and thus connected to the CC1 line or the CC2 line. For example, when communication is performed through the CC1 line of the first connector 421, the CC2 line of the first connector 421 may be used as a power supply pin (e.g., VCONN) that receives power. Alternatively, when communication is performed through the CC2 line of the first connector 421, the CC1 line of the first connector 421 may be used as the power supply pin that receives power. A detailed description of the CC1/CC2 line 421-2 will be made through FIG. 6A that illustrates a pin structure of the USB type C interface described below.

When a signal is detected through the VBUS line 421-1 or the CC1/CC2 line 421-2, the first PDIC 551 may turn on a first switch 553. As the signal is detected, the first PDIC 551 may recognize that the external device 410 is connected and notify the MCU 423 of the connection of the external device 410. The MCU 423 may determine that the external device 410 is connected to the first connector 421 based on the signal transferred from the first PDIC 551. That is, when the signal is received from the first PDIC 551, the MCU 423 may determine the charging scheme of the external device 410 to be the PD. The MCU 423 may receive a request for transmitting profile information from the external device 410 through the CC1/CC2 line 421-2. The profile information may include information on various levels of voltage or various levels of current of the power supply device 430. When the power supply device 430 is connected to the second connector 425 and the profile information of the power supply device 430 is stored in a RAM, the MCU 423 may transmit the profile information of the power supply device 430 to the external device 410 through the CC1/CC2 line 421-2.

The external device 410 according to an embodiment of the present disclosure may be charged with various levels of charging voltage or current, and may include a current limiter for preventing an overcurrent (or overvoltage). The current limiter may limit a maximum value of the supplied voltage or current such that the voltage or current is charged within a range in which the external device 410 is not damaged. Accordingly, the external device 410 may have a limit on a maximum voltage or a maximum current to prevent the overvoltage. The external device 410 may charge a battery with the voltage or current of the external device 410 by using the current limiter even though the charging voltage or the charging current provided from the power supply device 430 is high. When the charging voltage or the charging current provided from the power supply device 430 is low, it takes a long time to charge the external device 410 but it does not mean that charging does not occur. The one or more levels of charging voltage correspond to voltages utilized when the external device 410 is charged, and may be, for example, 5 V, 9 V, and 12 V. The one or more levels of charging current correspond to currents utilized when the external device 410 is charged, and may be, for example, 500 mA, 900 mA, 1 A, and 1.5 A. The external device 410 may determine the voltage or the current to be charged based on the profile information. The external device 410 may transmit charging request information including the voltage or the current to be charged to the electronic device 420.

When the power supply device 430 is connected to the second connector 425 according to an embodiment of the present disclosure, the second PDIC 552 may detect a signal through the VBUS line 425-1 or the CC1/CC2 line 421-2. When a signal is detected through the VBUS line 425-1 or the CC1/CC2 line 425-2, the second PDIC 552 may turn on a second switch 554. As the signal is detected, the second PDIC 552 may recognize that the power supply device 430 is connected and notify the MCU 423 of the connection of the power supply device 430. The MCU 423 may determine that the power supply device 430 is connected to the second connector 425 based on the signal transferred from the second PDIC 552. When the signal received from the second PDIC 552, the MCU 423 may determine the charging scheme of the power supply device 430 to be the PD. The MCU 423 may make a request for the profile information to the power supply device 430 through the CC1/CC2 line 425-2. The power supply device 430 may transmit its own profile information to the electronic device 420 in response to the request. When the profile information is received from the power supply device 430, the MCU 423 may store the profile information in the RAM.

When the first switch 553 is turned on and the second switch 554 is turned on, the VBUS line 421-1 of the first connector 421 and the VBUS line 425-1 of the second connector 425 may be connected to each other. That is, as a VBUS line 555 is connected between the first switch 553 and the second switch 554, the external device 410 may receive the current through the VBUS line from the power supply device 430.

The MCU 423, according to an embodiment, may detect the signal through the VBUS line 425-1 or the D+ line 425-3 and the D− line 425-4 of the second connector 425. The MCU 423 may determine that the power supply device 430 is connected through the D+ line 425-3 and the D− line 425-4 of the second connector 425. That is, when the signal is received through the D+ line 425-3 and the D− line 425-4, the MCU 423 may determine the charging scheme of the power supply device 430 to be the AFC or the QC. The MCU 423 may make a request for a profile to the power supply device 430 through the D+ line 425-3 and the D− line 425-4. The power supply device 430 may transmit its own profile information to the electronic device 420 in response to the request. When the profile information is received from the power supply device 430, the MCU 423 may store the profile information in the RAM.

When the charging scheme of the power supply device 430 is the PD charging scheme, the MCU 423 according to an embodiment of the present disclosure may communicate with the power supply device 430 through the CC1/CC2 line 425-2. When the charging scheme of the power supply device 430 is the AFC or QC charging scheme, the MCU 423 according to an embodiment of the present disclosure may communicate with the power supply device 430 through the D+ line 425-3 and the D− line 425-4. An operation of identifying the charging scheme of the MCU 423 according to an embodiment may be a design change matter. For example, the MCU 423 may first identify whether the charging scheme of the power supply device 430 is the QC charging scheme or the AFC charging scheme through the D+ line 425-3 and the D− line 425-4 and then identify whether the charging scheme of the power supply device 430 is the PD charging scheme through the CC1/CC2 line 425-2. In another example, the MCU 423 may first identify whether the charging scheme of the power supply device 430 is the PD charging scheme through the CC1/CC2 line 425-2 and then identify whether the charging scheme of the power supply device 430 is the AFC charging scheme or the AFC charging scheme through the D+ line 425-3 and the D− line 425-4.

The power supply device 430 according to an embodiment of the present disclosure may transmit its own profile information to the electronic device 420 in response to the request. For example, the profile information may include at least one of an identifier of the power supply device 430, a protocol (e.g., charging scheme), one or more levels of charging voltage, and one or more levels of charging current. The power supply device 430 is the charger and thus may provide various levels of voltage or current. For example, the power supply device 430 may provide a normal charging voltage or a high speed charging voltage. The normal charging voltage (e.g., 5 V) may be lower than the high speed charging voltage (e.g., 9 V, 12 V, or 20 V). Further, the power supply device 430 may provide a normal charging current or a high speed charging current. The normal charging current (e.g., 500 mA) may be lower than the high speed charging current (e.g., 900 mA, 1 A, 1.5 A, 2 A, or 3 A). The MCU 423 may store the received profile information of the power supply device 430 in the RAM. The storing of the information of the power supply device 430 in the RAM may be to transmit the profile information of the power supply device 430 to the external device 410 when the external device 410 is connected to the electronic device 420.

The external device 410 according to an embodiment of the present disclosure may determine the voltage or current to be charged based on the profile information received from the electronic device 420. The external device 410 may transmit charging request information including the voltage or the current to be charged to the electronic device 420. For example, the profile information may be 5 V/500 mA, 9 V/900 mA, and 12 V/1.5 A and include information on various levels of voltage or current. The external device 410 may select a voltage or current level (e.g., 9 V/900 mA) to be charged, from the profile information. The external device 410 may transmit the information on the selected voltage or current (e.g., 9 V/900 mA) to the electronic device 420 as "charging request information." The MCU 423 may receive the charging request information from the external device 410 and transfer the charging request information to the power supply device 430. The power supply device 430 may provide the current based on the charging request information. For example, when the charging request information is received, the power supply device 430 may supply the current of 900 mA to the electronic device 420. The electronic device 420 may transfer the current provided from the power supply device 430 to the external device 410.

FIG. 5C illustrates an example of a charging path between the external device and the power supply device based on a charging scheme according to various embodiments.

Referring to FIG. 5C, the control circuit 423 may set a charging path 560 between the external device and the power supply device according to a charging scheme. When the charging scheme of the external device 410 is the same as the charging scheme of the power supply device 430, the control circuit 423 may set the charging path between the external device 410 and the power supply device 430 as a "first charging path." When the charging scheme is the "PD," an electrically conductive path may be formed through a PDIC (e.g., PDIC 1 or PDIC 2). That is, when the electrically conductive path is formed through the CC1 line or the CC2 line, the PDIC may be included between the connectors (e.g., the first and second connector 421 or 425) and the control circuit 423.

For example, the first charging path may correspond to an electrically conductive path 561 formed between the CC1 line of the first connector 421 and the CC1 line of the second connector 425. For example, when the electrically conductive path 561 is formed as the first charging path, the CC1 line of the first connector 421 may be the line (e.g., VCONN) that receives power. In this case, the CC2 line of the first connector 421 and the CC2 line of the second connector 425 may be a communication path for transferring the signal. That is, when the CC1 line is used as the line for power supply, the remaining CC2 line may be used as the line for communication. Further, the power supply is possible through the VBUS line. That is, the electrically conductive path may be formed between the VBUS line of the first connector 421 and the VBUS line of the second connector 425, and the power supply device 430 may provide the current to the external device 410 through the electrically conductive path.

Alternatively, the first charging path may correspond to an electrically conductive path 562 formed between the CC1 line of the first connector 421 and the CC2 line of the second connector 425. For example, when the electrically conductive path 562 is formed as the first charging path, the CC1 line of the first connector 421 may be the line (e.g., VCONN) that receives power. In this case, the CC2 line of the first connector 421 and the CC1 line of the second connector 425 may be a communication path for transferring the signal. Further, the power supply is possible through the VBUS line.

Alternatively, the first charging path may correspond to an electrically conductive path 563 formed between the CC2 line of the first connector 421 and the CC1 line of the second connector 425. For example, when the electrically conductive path 563 is formed as the first charging path, the CC2 line of the first connector 421 may be the line (e.g., VCONN) that receives power. In this case, the CC1 line of the first connector 421 and the CC2 line of the second connector 425 may be a communication path for transferring the signal. Further, the power supply is possible through the VBUS line.

Alternatively, the first charging path may correspond to an electrically conductive path 564 formed between the CC2 line of the first connector 421 and the CC2 line of the second connector 425. For example, when the electrically conductive path 564 is formed as the first charging path, the CC2 line of the first connector 421 may be the line (e.g., VCONN) that receives power. In this case, the CC1 line of the first connector 421 and the CC1 line of the second connector 425 may be a communication path for transferring the signal. Further, the power supply is possible through the VBUS line.

When the charging scheme of the external device 410 is different from the charging scheme of the power supply device 430, the control circuit 423 according to an embodiment of the present disclosure may set the charging path between the external device 410 and the power supply device 430 as a "second charging path." For example, when the charging scheme of the external device 410 is the "PD" and the charging scheme of the power supply device 430 is the "AFC" or the "QC," that is, when the charging schemes are different, the control circuit 423 may set a second charging path. The second charging path may correspond to an electrically conductive path 565 formed between the CC1 line of the first connector 421 and the D+ line or the D− line of the second connector 425. For example, when the electrically conductive path 565 is formed as the second charging path, the CC1 line of the first connector 421 may be the line (e.g., VCONN) that receives power. Further, the power supply is possible through the VBUS line.

Alternatively, the second charging path may correspond to an electrically conductive path 566 formed between the CC2 line of the first connector 421 and the D+ line or the D− line of the second connector 425. For example, when the electrically conductive path 566 is formed as the second charging path, the CC2 line of the first connector 421 may be the line (e.g., VCONN) that receives power. Further, the power supply is possible through the VBUS line. Accordingly, according to the present disclosure, even though the charging scheme of the external device 410 is different from the charging scheme of the power supply device 430, the external device 410 may be charged with the current supplied from the power supply device 430.

An electronic device according to various embodiments may include a first connector including a first number of conductive pins arranged according to a first protocol, a second connector including a second number of conductive pins arranged according to a second protocol different from the first protocol, the second number being different from the first number, and a control circuit connected to the first connector and the second connector, wherein the control circuit may be connected to an external device through at least one of the first number of conductive pins, and configured to receive profile information indicating a capability of a power supply device connected to the second connector through at least one of the second number of conductive pins or an identification of an external device, and to set a charging path between the first connector and the second connector by using the conductive pin connected to the external device and the conductive pin connected to the power supply device.

The conductive pin connected to the external device is a CC1 pin or a CC2 pin, and the conductive pin connected to the power supply device may include one of the CC1 pin and the CC2 pin, a D+ pin, and a D− pin.

When the conductive pin connected to the external device and the conductive pin connected to the power supply device correspond to the CC1 pin or the CC2 pin, the control circuit may be configured to set a first charging path to form an electrically conductive path between the CC1 pin or the CC2 pin of the first connector and the CC1 pin or the CC2 pin of the second connector.

When the conductive pin connected to the external device is the CC1 pin or the CC2 pin and the conductive pin connected to the power supply device is the D+ pin and the D− pin, the control circuit may be configured to set a second charging path to form an electrically conductive path between the CC1 pin or the CC2 pin of the first connector and the D+ pin and the D− pin of the second connector.

When the conductive pin connected to the power supply device is the CC1 pin or the CC2 pin, the control circuit may be configured to determine that a charging scheme of the power supply device corresponds to Power Delivery (PD).

When the conductive pin connected to the power supply device is the D+ pin and the D− pin, the control circuit may be configured to determine that a charging scheme of the power supply device corresponds to Adaptive Fast Charging (AFC) or Quick Charge (QC).

The profile information may be configured to allow provision of voltages at multiple levels for charging.

The electronic device may further include a third connector including a third number of conductive pins arranged according to a third protocol different from the first protocol and the second protocol, the third number being different from the first number and the second number, wherein the control circuit may be electrically connected to the third connector and configured to provide a signal transmitted from the external device through at least one of the third number of conductive pins.

The third connector may be configured to include at least one of a USB 2.0 type A connector, a High Definition Multimedia Interface (HDMI) terminal, Audio/Video (A/V) output terminal, and a memory card recognition terminal.

The electronic device may further include a fourth connector including a fourth number of conductive pins arranged according to a fourth protocol, wherein the control circuit may be electrically connected to the fourth connector and configured to pass a signal transmitted from the external device to the fourth connector.

The control circuit may be configured to form an electrically conductive path for data communication between the first connector and the fourth connector.

FIGS. 6A to 6D illustrate a USB 3.1 type C interface according to various embodiments.

Figure 6A:
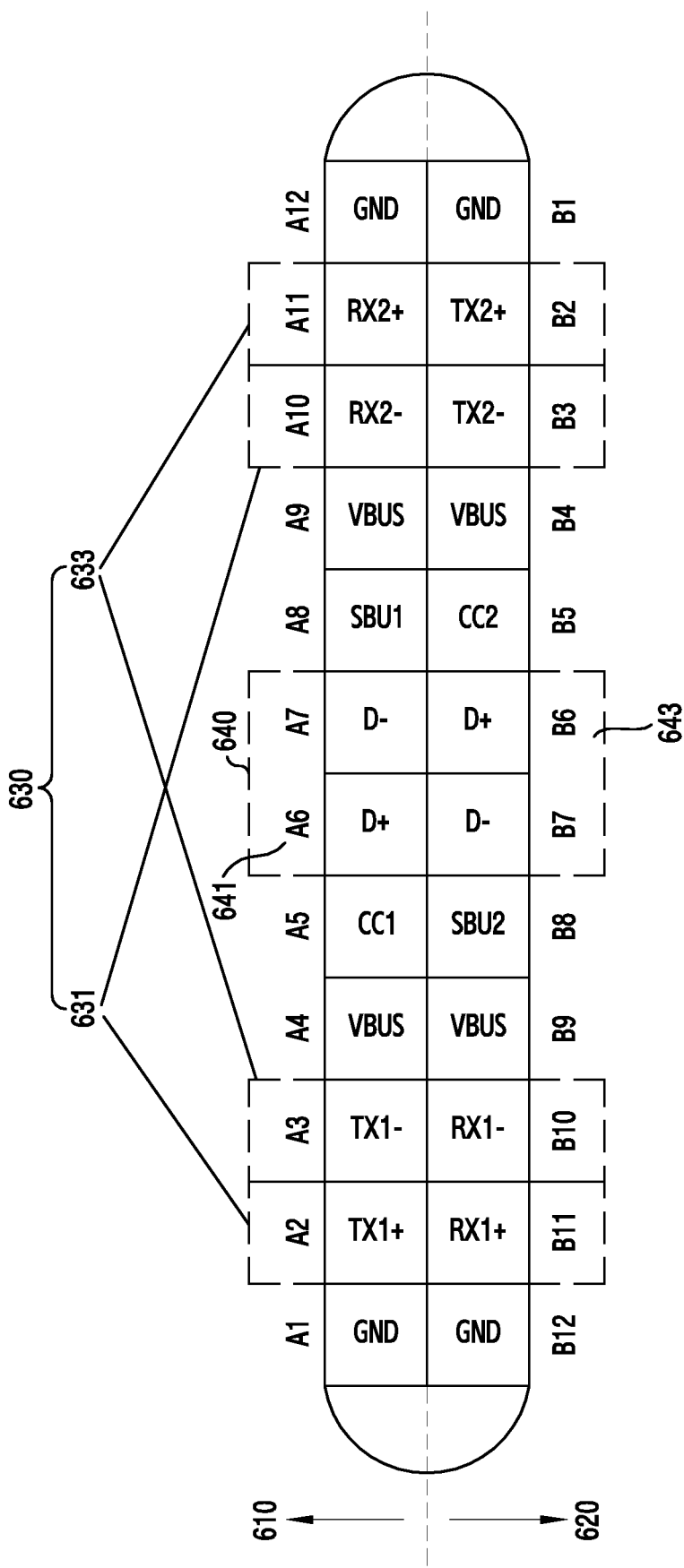
FIG. 6A, FIG. 6B, FIG. 6C and FIG. 6D illustrate a USB 3.1 type C interface according to various embodiments.
Figure 6B:
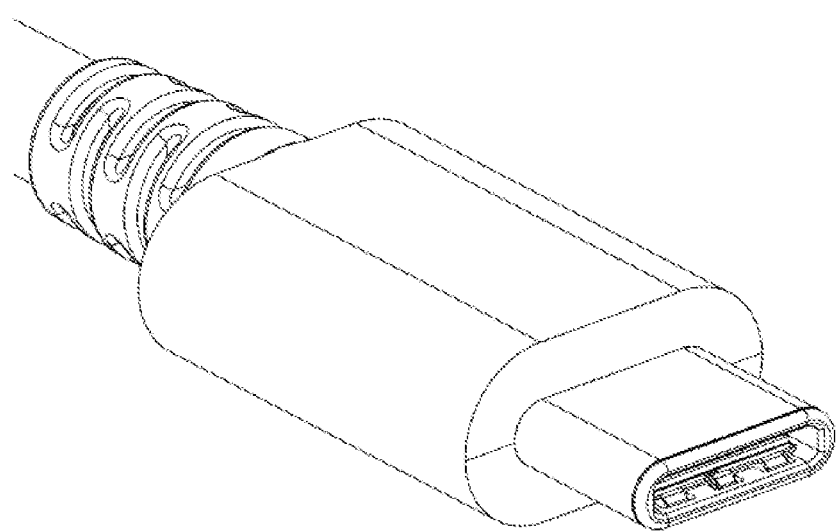

FIG. 6A illustrates an example for describing a function of conductive pins included in a USB type C connector. FIG. 6B illustrates an appearance of a USB type C interface and FIG. 6C illustrates an example of a structure in which function pins of the USB type C interface are arranged.

Figure 6C:
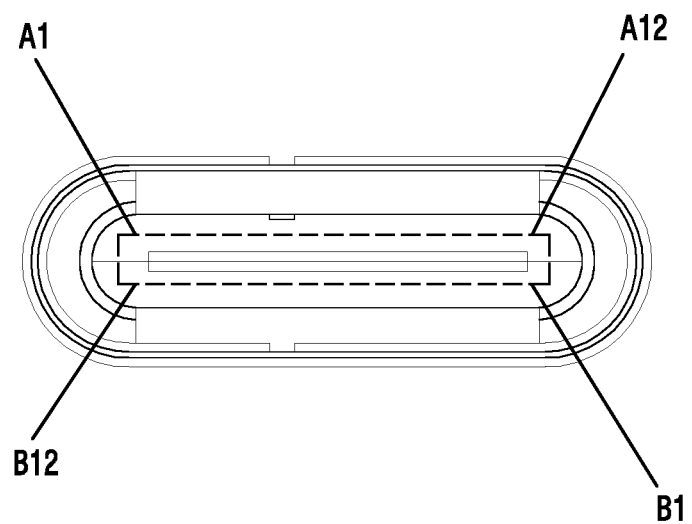

Referring to FIGS. 6A to 6C, an input/output pin out structure of the USB type C connector may be separated into a first part 610 and a second part 620, and the first part 610 and the second part 620 may have a symmetrical structure. The USB interface (e.g., USB connector) of the electronic device may be connected to a USB cable of a particular gender based on the symmetrical structure, regardless of directivity. For example, since connectors at both ends of the USB cable may have the same shape (form), and the connector does not distinguish between top and bottom, immediate connection is possible without the need to match pin directivity of the connector. According to an embodiment, the USB interface may be connected right-side-up (e.g., by placing the first part 610 disposed towards a top of the connector) or, inversely, the USB interface may be connected upside-down (by placing the first part 610 disposed towards a bottom of the connector). A connection state may be detected through Configuration Channels (CCs) (e.g., CC1 as seen in the A5 pin) or CC2 as seen in the B5 pin). When "pull-down" (Rd) is detected in CC1 (e.g., A5 pin) of the USB interface, it may be determined that the first part 610 is in a plugged-in state. When pull-down is detected in CC2 (B5 pin) of the USB interface, the second part 620 may be in a plugged-in state.

The USB interface may include, for example, a total of 24 designated pins (e.g., A1 to A12 and B1 to B12), and each of the 24 pins may have its own role as illustrated in FIG. 6A.

The USB interface may support, for example, data communication at different transmission rates. For example, the USB interface may include a first communication path 630 corresponding to a first standard (e.g., USB 3.1 protocol) supporting a highest speed data communication that is available, and a second communication path 640 corresponding to a second standard (e.g., USB 2.0 protocol) supporting lowest speed data communication among those available. The first communication path 630 of the first standard (e.g., USB 3.1) may include a pair 631 of TX1+ (A2) and RX2-(A10) or a pair 633 of TX1-(A3) and RX2+ (A11) in the first part 610 (as depicted in FIG. 6A). Alternatively, the first communication path 630 of the first standard (e.g., USB 3.1) may include a pair 631 of TX1+ (A2) and RX2-(A10) or a pair 633 of TX1-(A3) and RX2+ (A11) in the second part 620 (which is not depicted in FIG. 6A). The second communication path 640 of the second standard (e.g., USB 2.0) may include a pair 641 of D+(A6) and D−(A7) in the first part 610 and another pair 643 of D+(B6) and D−(B7) in the second part 620. That is, the first communication path 630 and the second communication path 640 may be symmetrically implemented in the first part 610 and the second part 620 in accordance with the symmetrical structure of the USB interface.

When the electronic devices are connected to each other through the USB interface, the electronic devices may operate as the host (e.g., Downstream Facing Port: DFP) or the device (or slave) (e.g., Upstream Facing Port: UFP) and whether to operate as the host or the slave may be determined through the Configuration Channels (CC) (e.g., CC1 or CC2) terminal of the USB interface. For example, in a connection method using the USB interface, CC1 and CC2 for connector coupling direction recognition and digital data communication exist and their roles may be defined as the host (DFP) and the device (UFP) by pull-up (Rp) or a current source and pull-down (Rd). In the USB interface, a pull-down (Rd) side may be defined as the device (UFP), and the host (DFP) may supply power through a power supply pin (e.g., VBUS or VCONN) according to a need of the device (UFP).

Further, the electronic devices may operate as a Dual Role Port (DRP) as well as the host (DFP) and the device (UFP). The DRP may indicate a mode (function) in which the roles of the host (DFP) and the device (UFP) of the electronic device can be adaptively changed. For example, when the DRP is connected as the host (DFP), the DRP may be changed to the device (UFP). When the DRP is connected as the device (UFP), the DRP may be changed to the host (DFP). Further, when two DRP are connected together, for example, one DRP may serve as the host (DFP) and the other DRP may serve as the device (UFP) in a random manner. For example, the electronic device such as a smart phone or a PC may serve as both the host (DFP) and the device (UFP) and thus periodically toggle pull-up and pull-down.

The VBUS of the USB interface may indicate a power supply terminal and support power corresponding to each USB standard illustrated in Table 1 below.

TABLE 1

| Mode of Operation | Nominal Voltage | Maximum Current | Notes |
| --- | --- | --- | --- |
| USB 2.0 | 5 V | 500 mA | Default Current, based on definitions in the base specifications |
| USB 3.1 | 5 V | 900 mA | Legacy charging |
| USB BC 1.2 | 5 V | Up to 1.5 A | Supports higher power devices |
| USB Type-C Current @ 1.5 A | 5 V | 1.5 A | Supports higher power devices |
| USB Type-C Current @ 3.0 A | 5 V | 3 A | Supports higher power devices |
| USBPD | Configurable up to 20 V | Configurable up to 5 A | Directional control and power level management |

As shown in Table 1 above, the USB interface according to various embodiments may support power capability up to 5 V/3 A. When USB Power Delivery (PD) is combined with the USB type C, the USB interface may support power capability up to 20 V/5 A. A USB PD protocol may be transmitted through a CC line connection. For example, the USB PD protocol may be transmitted through CC1 (A5) when the connection is made with the first part 610, and the USB PD protocol may be transmitted through CC2 (B5) when the connection is made with the second part 620.

In general, when the electronic devices are designated as the host (DFP) and the device (UFP), the electronic device operating as the host (DFP) may transfer data to the electronic device operating as the device (UFP) and first transmit data through the transmission terminal of the first standard (e.g., USB 3.1) having two pairs of pins (e.g., the first communication path 630) in the USB interface. Alternatively, when the electronic device is not compatible with the first standard, data may be transmitted through the transmission terminal of the second standard (e.g., USB 2.0) having one pair of pins (e.g., the second communication path 640).

For example, the USB interface may include data communication paths corresponding to different standards (e.g., the first standard and the second standard) for data transmission as described above. According to an embodiment, the USB interface may be divided into the first communication path 630 for data communication (e.g., SuperSpeedPlus (SSP), 10 Gbps communication) based on a communication speed according to the first standard (e.g., USB 3.1) and the second communication path 640 for data communication (e.g., high speed, 480 Mbps) based on a communication speed according to the second standard (e.g., USB 2.0). When the electronic devices are connected through the USB interface and the electronic device operating as the host (DFP) transmits data to the electronic device operating as the device (UFP), data communication may be performed preferentially through the first communication path 630 of the first standard having a higher priority (e.g., higher communication speed) (e.g., the path of the standard having a higher data transmission rate is first set).

Meanwhile, in the USB interface, all data connections and controls are defined to exchange digital signals through CC1 and CC2 and, accordingly, a gender is needed for a connection to the power supply device 430 that supports the USB 2.0 type A connector.

According to various embodiments, the gender may be needed for compatibility of the interface between a legacy device using a lower standard interface (e.g., USB 2.0) and an electronic device using a higher standard interface (e.g., USB 3.1).

Figure 6D:
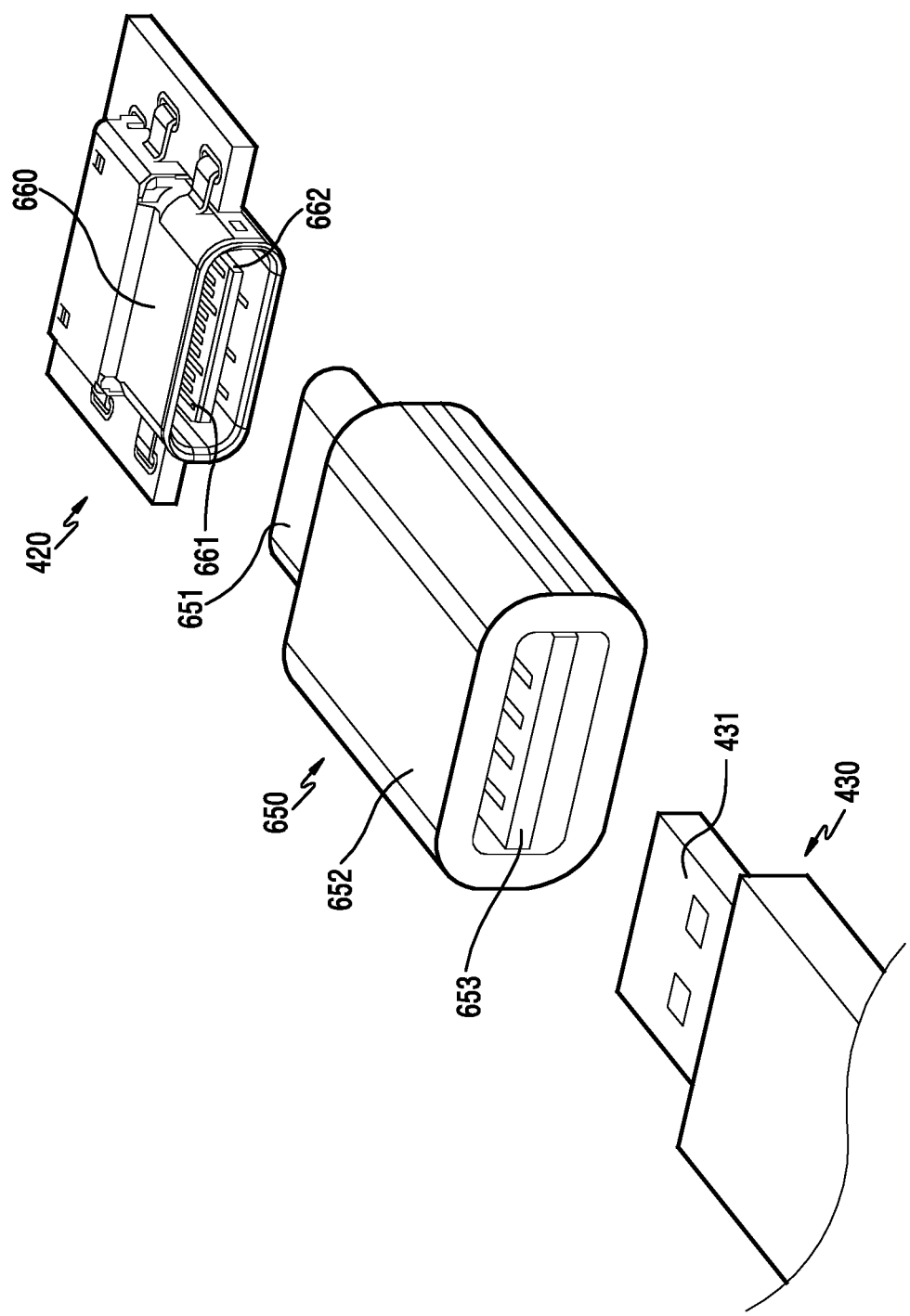

FIG. 6D illustrates an example for connecting the USB 2.0 type A connector and the USB 3.1 type C connector by using the gender according to various embodiments.

Referring to FIG. 6D, the power supply device 430 may include the connector 431 that supports the USB 2.0 interface such as Micro A, B, AB, and the like. The electronic device 420 may include a connector 662 that supports the USB 3.1 type C interface and a predetermined number of pins 661 (e.g., y number (e.g., 24) of pins) within a housing 660. The connector 431 of the power supply device 430 may have a form of the USB 2.0 type A connector, and the connector 662 of the electronic device 420 may have a form of the USB 3.1 type C connector. The connector 431 may have an asymmetrical shape (e.g., up and down asymmetrical shape in the micro USB) in at least one direction. For example, the connector 431 may be a male connector. The connector 662 may have a symmetrical structure, and a connection thereof is possible regardless of directivity between connectors. For example, the connector 662 may be a female connector.

In this case, since shapes of the two connectors are different, a gender adaptor 650 is needed to connect the two connectors. The gender adaptor 650 may include a first connector 653 that supports the USB 2.0 type A interface and a second connector 651 that supports the USB 3.1 type C interface. The gender adaptor 650 may include a housing 652 (e.g., body) including various circuits for an electrical connection between the first connector 653 and the second connector 651. Accordingly, the connector 662 of the electronic device 420 may be connected to the power supply device 430 having the connector 431 of the USB 2.0 type A through the gender adaptor 650.

Although it is illustrated that the connector 431 of the power supply device 430 corresponds to the USB 2.0 type A connector as example in the drawings, the connection with the electronic device 420 may be performed through the gender adaptor 650 in a case where the connector of the external device 410 is the USB 2.0 type A connector.

Figure 7:
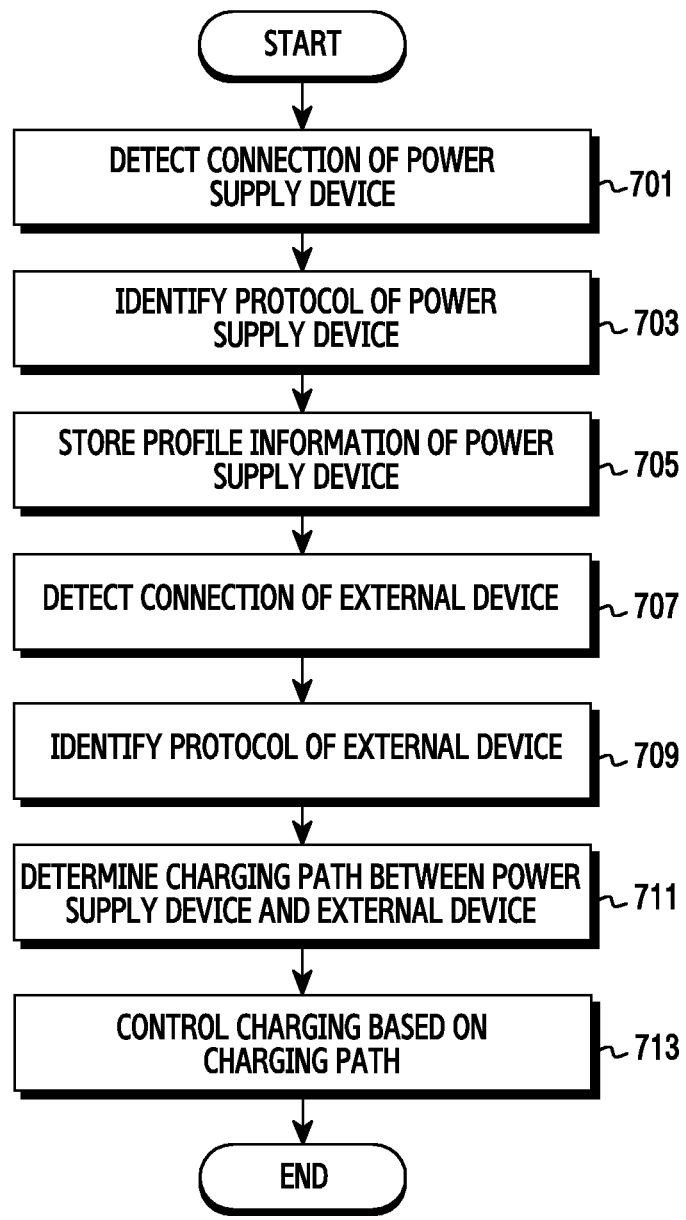
FIG. 7 is a flowchart illustrating an operation method of the electronic device according to various embodiments.

FIG. 7 is a flowchart illustrating an operation method of the electronic device according to various embodiments.

Referring to FIG. 7, in operation 701, the electronic device 420 (e.g., the control circuit 423) may detect a connection of the power supply device 430. The electronic device 420 may refer to the electronic device 420 of FIG. 4, and the control circuit 423 may refer to the MCU 423. When a signal is detected through at least one of the VBUS line, the CC1 line, and the CC2 line of the connector (e.g., the second connector 425), the control circuit 423 may detect that the power supply device 430 is connected to the second connector 425. Alternatively, when a signal is detected through the VBUS line, or the D+ line and D− line of the second connector 425, the control circuit 423 may detect that the power supply device 430 is connected to the second connector 425.

In operation 703, the control circuit 423 may identify a protocol of the power supply device 430. When it is determined that the power supply device 430 is connected, the control circuit 423 may form an electrically conductive path with the power supply device 430. As the control circuit 423 detects a signal for the connection with the power supply device 430 through any pin (e.g., CC1, CC2, D+, and D−) of the second connector 425, the control circuit 423 may identify the protocol of the power supply device 430. For example, when it is determined that the control circuit 423 is connected the power supply device 430 through the CC1 line or the CC2 line of the second connector 425, the control circuit 423 may determine that the charging scheme of the power supply device 430 is the "PD." Further, when it is determined that the control circuit 423 is connected to the power supply device 430 through the D+ line and D− line of the second connector 425, the control circuit 423 may determine that the charging scheme of the power supply device 430 is the "AFC" or the "QC."

When the charging scheme of the power supply device 430 is the "PD," the control circuit 423 according to an embodiment of the present disclosure may make a request for a profile to the power supply device 430 through the CC1 line or the CC2 line of the second connector 425, and receive profile information of the power supply device 430 from the power supply device 430 in response to the request. That is, the control circuit 423 may communicate with the power supply device 430 through the CC1 line or the CC2 line. When the charging scheme of the power supply device 430 is the "AFC" or the "QC," the control circuit 423 according to an embodiment of the present disclosure may make a request for a profile to the power supply device 430 through the D+ line and D− line of the second connector 425 and receive profile information of the power supply device 430 from the power supply device 430 in response to the request. That is, the control circuit 423 may communicate with the power supply device 430 through the D+ line and D− line.

The protocol information may correspond to identifying an identification or a capability of the power supply device 430. The protocol information may include at least one of an identifier, a protocol, one or more levels of charging voltage, and one or more levels of charging current of the power supply device 430. For example, the power supply device 430 may provide various levels of voltage such as 5 V, 9 V, 12 V, and 20 V, and provide various levels of current such as 500 mA, 900 mA, 1 A, 1.2 A, 2 A, and 3 A.

For example, when the identification or the capability is completely identified with the power supply device 430, the control circuit 423 may maintain the connection with the power supply device 430 at a voltage (e.g., standby voltage) lower than a charging voltage of the power supply device 430. For example, when the identification or the capability is completely identified with the power supply device 430, the control circuit 423 may receive the current from the power supply device 430 through the VBUS line of the second connector 425. When the identification or the capability is completely identified with the power supply device 430, the control circuit 423 may instruct the power supply device 430 to stand by the charging. The power supply device 430 may maintain a charging standby state according to the instruction.

In operation 705, the control circuit may store the profile information of the power supply device 430 in the memory 130. The control circuit 423 may store a list of voltages and currents, which can be provided by the power supply device 430, in the memory 130 (e.g., RAM) as the profile of the power supply device 430. For example, the control circuit 423 may store information on a minimum voltage (or current) and a maximum voltage (or current), which can be provided by the power supply device 430, as the profile of the power supply device 430.

In operation 707, the control circuit 423 may detect the connection of the external device 410. For example, when a signal is detected through at least one of the VBUS line, the CC1 line, and the CC2 line of the connector (e.g., the first connector 421), the control circuit 423 may detect that the external device 410 is connected to the first connector 421.

In operation 709, the control circuit 423 may identify a protocol of the external device 410. When it is determined that the external device 410 is connected, the control circuit 423 may form an electrically conductive path with the external device 410. As a signal for the connection with the external device 410 is detected through any pin (e.g., CC1, CC2, D+, or D−) of the first connector 421, the control circuit 423 may identify the protocol of the external device 410. For example, when it is determined that the external device 410 is connected through the CC1 line or the CC2 line of the first connector 421, the control circuit 423 may determine that the charging scheme of the external device 410 is the "PD." When the charging scheme of the external device 410 is the "PD," the control circuit 423 according to an embodiment of the present disclosure may receive a request for profile information from the external device 410 through the CC1 line or the CC2 line of the first connector 421. The profile may refer to profile information of the power supply device 430. The control circuit 423 may transmit the profile information stored in the RAM to the external device 410 in response to the request. The external device 410 may receive the profile information and determine a charging voltage or current to be charged, based on the profile information. The external device 410 may transmit charging request information including the determined charging voltage or current to the electronic device 420. For example, when the CC1 line of the first connector 421 is used as a communication path for making a request for the profile and receiving information, the CC2 line of the first connector 421 may be used as a power supply line (e.g., VCONN). Alternatively, when the CC2 line of the first connector 421 is used as a communication path for making a request for the profile and receiving information, the CC1 line of the first connector 421 may be used as a power supply line (e.g., VCONN).

For example, when the identification or the capability is completely identified with the external device 410, the control circuit 423 may maintain the connection with the external device 410 at a voltage (e.g., standby voltage) lower than a charging voltage of the external device 410. When operations 707 to 709 are performed before operations 701 to 705, the external device 410 may provide the current to the electronic device 420. In this case, the control circuit 423 may receive the current from the external device 410 through the VBUS line of the first connector 421. Whether the external device 410 receives or provides power may be determined by definition of roles of a host (DFP) and a device (UFP) by pull-up (Rp) of the CC1 line and the CC2 line of the first connector 421 or a current source and pull-down (Rd). When the identification or the capability is completely identified with of the external device 410, the control circuit 423 may instruct the external device 410 to stand by the charging. The external device 410 may maintain the charging standby state according to the instruction.

Although FIG. 7 illustrates that operations 707 to 709 are performed after operations 701 to 705, operations 701 to 705 may be performed after operations 707 and 709. Alternatively, operations 701 to 705 may be performed simultaneously with operations 707 and 709. For convenience of the description, only an example for sequentially connecting devices to the connector has been described, and the present is not limited to first performance of any operation.

In operation 711, the control circuit 423 may determine a charging path between the power supply device 430 and the external device 410. According to an embodiment, the control circuit 423 may determine whether the protocol of the external device 410 is the same as the protocol of the power supply device 430. For example, when charging schemes of the protocol of the external device 410 and the protocol of the power supply device 430 correspond to the PD charging scheme, the control circuit 423 may determine the charging path between the power supply device 430 and the external device 410 as a first charging path. For example, the first charging path means that the electrically conductive path is formed between the CC1 line or the CC2 line of the first connector 421 and the CC1 line or the CC2 line of the second connector 425.

When the protocol (e.g., USB 3.1 protocol) of the external device 410 according to an embodiment of the present disclosure is different from the protocol (e.g., USB 2.0 protocol) of the power supply device 430, the control circuit 423 may determine the charging path between the power supply device 430 and the external device 410 as a second charging path. In this case, the charging scheme of the external device 410 may be the PD charging scheme, and the charging scheme of the power supply device 430 may be the AFC or the QC. For example, the second charging path means that the electrically conductive path is formed between the CC1 line or the CC2 line of the first connector 421 and the D+ line and D− line of the second connector 425.

Further, an operation for determining the charging path may include an operation for negotiating the charging voltage or the charging current between the power supply device 430 and the external device 410. Alternatively, the control circuit 423 may receive charging request information from the external device 410 and transmit the received charging request information to the power supply device 430 between operations 709 and 711 or after operation 711. For example, the external device 410 may select 9 V/900 mA as the voltage or current to be charged from the profile information. The external device 410 may transmit the information on the selected voltage or current (e.g., 9 V/900 mA) to the electronic device 420 as "charging request information." The power supply device 430 may receive the charging request information through the electronic device 420 and provide the current based on the charging request information.

According to an embodiment, the power supply device 430 may change a level of the voltage or current based on the charging request information received from the electronic device 420. For example, when the voltage of 3 V or 5 V (500 mA) is supplied after the power supply device 430 has completed the identification with the electronic device 420, the power supply device 430 may boost the voltage to 9 V (900 mA) according to the charging request information and provide the boosted voltage.

In operation 713, the control circuit 423 may control the charging based on the charging path. For example, when the protocol of the external device 410 is the same as the protocol of the power supply device 430, the control circuit 423 may provide the current supplied from the power supply device 430 to external device 410 through the first charging path. When the protocol of the external device 410 is different from the protocol of the power supply device 430, the control circuit 423 may provide the current supplied from the power supply device 430 to external device 410 through the second charging path. Accordingly, even though the charging scheme of the power supply device 430 is different from the charging scheme of the external device 410, the electronic device 420 may charge the external device 410 with the voltage supplied from the power supply device 430.

Figure 8:
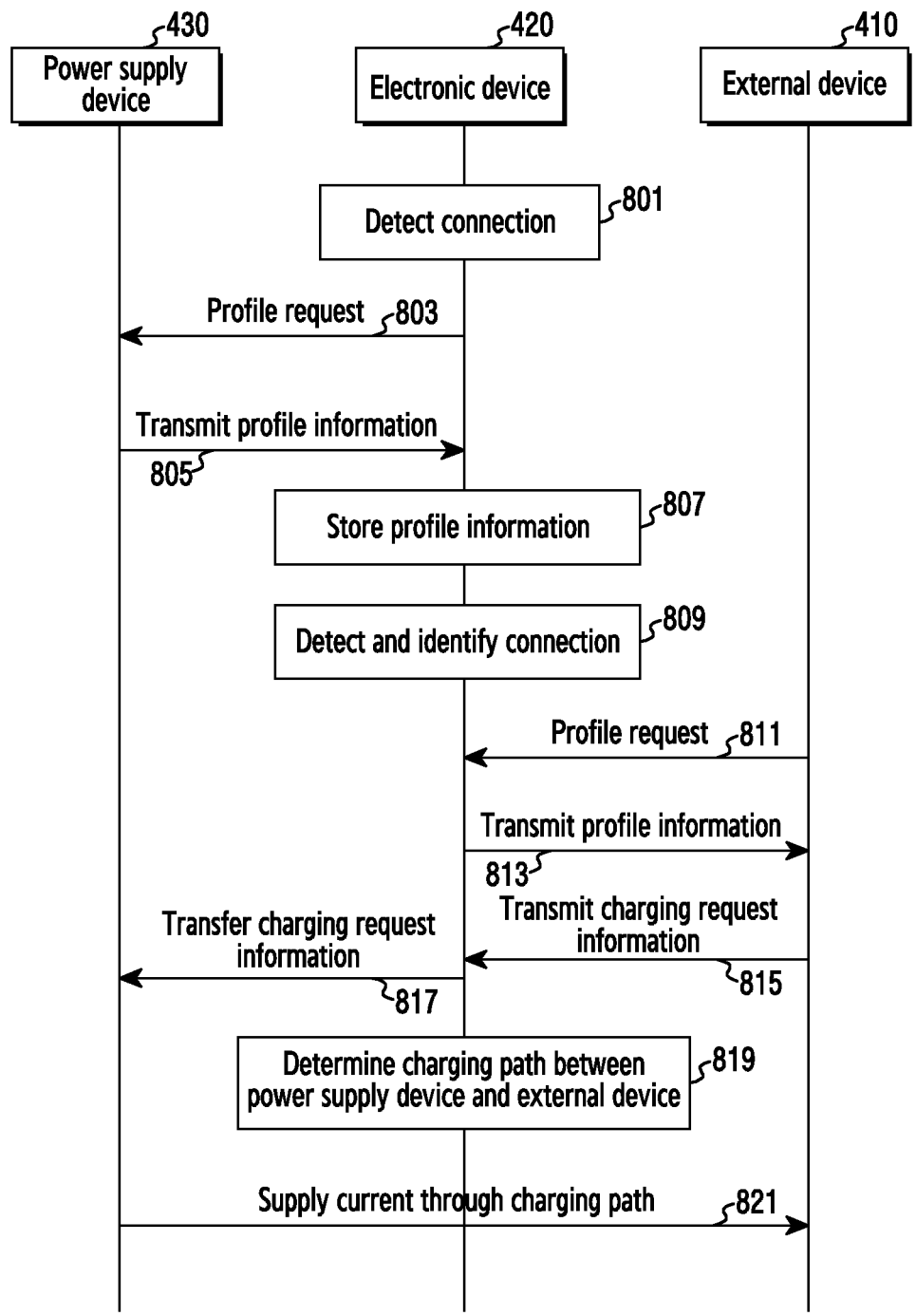
FIG. 8 is a flowchart illustrating an operation method between the electronic device and external devices according to various embodiments.

FIG. 8 is a flowchart illustrating an operation method between the electronic device and external devices according to various embodiments.

Referring to FIG. 8, in operation 801, the electronic device 420 may detect connection of the external device. When a signal is detected in at least one of the VBUS line, the CC1 line, and the CC2 line of the connector (e.g., second connector 425), the electronic device 420 may detect that the external device is connected. The external device may be the power supply device 430. Alternatively, when a signal is detected through the VBUS line, or the D+ line and D− line of the second connector 425, the electronic device 420 may detect that the power supply device 430 is connected to the second connector 425. For example, when it is determined that the electronic device 420 is connected the power supply device 430 through the CC1 line or the CC2 line of the second connector 425, the electronic device 420 may determine that the charging scheme of the power supply device 430 is the "PD." Further, when it is determined that the electronic device 420 is connected the power supply device 430 through the D+ line and D− line of the second connector 425, the electronic device 420 may determine that the charging scheme of the power supply device 430 is the "AFC" or the "QC."

In operation 803, the electronic device 420 may make a request for a profile to the power supply device 430 connected to the second connector 425. The profile may be for identifying an identification or a capability of the power supply device 430.

In operation 805, the power supply device 430 may transmit its own profile information to the electronic device 420 in response to the information request. The profile information may include at least one of an identifier of the power supply device 430, one or more levels of charging voltage information, and one or more levels of charging current information.

In operation 807, the electronic device 420 may receive the profile information of the power supply device 430 from the power supply device 430 and store the received profile information in the RAM. The electronic device 420 may instruct the power supply device 430 to wait for the charging after storing the information of the power supply device 430 in the RAM.

In operation 809, the electronic device 420 may detect and identify the connection of the external device 410. For example, when a signal is detected through at least one of the VBUS line, the CC1 line, and the CC2 line of the connector (e.g., the first connector 421), the electronic device 420 may detect that the external device 410 is connected to the first connector 421.

For example, when it is determined that the external device 410 is connected through the CC1 line or the CC2 line of the first connector 421, the control circuit 423 may determine that the charging scheme of the external device 410 as the "PD".

In operation 811, the external device 410 may make a request for the profile to the electronic device 420. The profile may correspond to a request for profile information of the power supply device 430 to charge the external device 410.

In operation 813, the electronic device 420 may transmit the profile information stored in the RAM to the external device 410 in response to the request. In operation 815, the external device 410 may receive the profile information from the electronic device 420 and select a charging voltage or a charging current to be charged, based on the profile information. The external device 410 may select 9 V/900 mA as the voltage or current to be charged, from the profile information.

Although FIG. 8 illustrates that operation 809 is performed after operations 801 to 807, operations 801 to 807 may be performed after operations 809 and 811. When operations 809 and 811 are first performed, there is no power supply device 430 connected to the electronic device 420, so that operation 813 may be performed after the connection of the power supply device 430. For convenience of the description, only an example for sequentially connecting devices to the connector has been described, and the present is not limited to first performance of any operation.

Operations 815 and 817 may be for determining the voltage or current when power is supplied between the external device 410 and the power supply device 430.

In operation 815, the external device 410 may transmit charging request information to the electronic device 420. The external device 410 may transmit the information on the selected voltage or current (e.g., 9 V/900 mA) to the electronic device 420 as "charging request information".

In operation 817, the electronic device 420 may receive the charging request information from the external device 410 and transfer the received charging request information to the power supply device 430. The power supply device 430 may provide the current based on the charging request information.

In operation 819, the electronic device 420 may determine a charging path between the external device 410 and the power supply device 430. For example, when the protocol (e.g., PD charging scheme) of the external device 410 is the same as the protocol (e.g., PD charging scheme) of the power supply device 430, the control circuit 423 may provide the current supplied from the power supply device 430 to external device 410 through the first charging path. When the protocol (e.g., AFC or QC charging scheme) of the power supply device 430 is different from the protocol (e.g., PD charging scheme) of the external device 410, the control circuit 423 may provide the current supplied from the power supply device 430 to external device 410 through the second charging path.

In operation 821, the external device 410 may receive the current supplied from the power supply device 430 and charge a battery by using the current. For example, when the power supply device 430 provides the current of 900 mA based on the charging request information, the electronic device 420 may charge the external device 410 by transferring the provided current to the external device 410. According to some embodiments, the external device 410 may receive a portion of the current among a total current provided from the power supply device 430. For example, when the current of 2 A is provided from the power supply device 430, the external device 410 may receive a current of 1.5 A.

Figure 9:
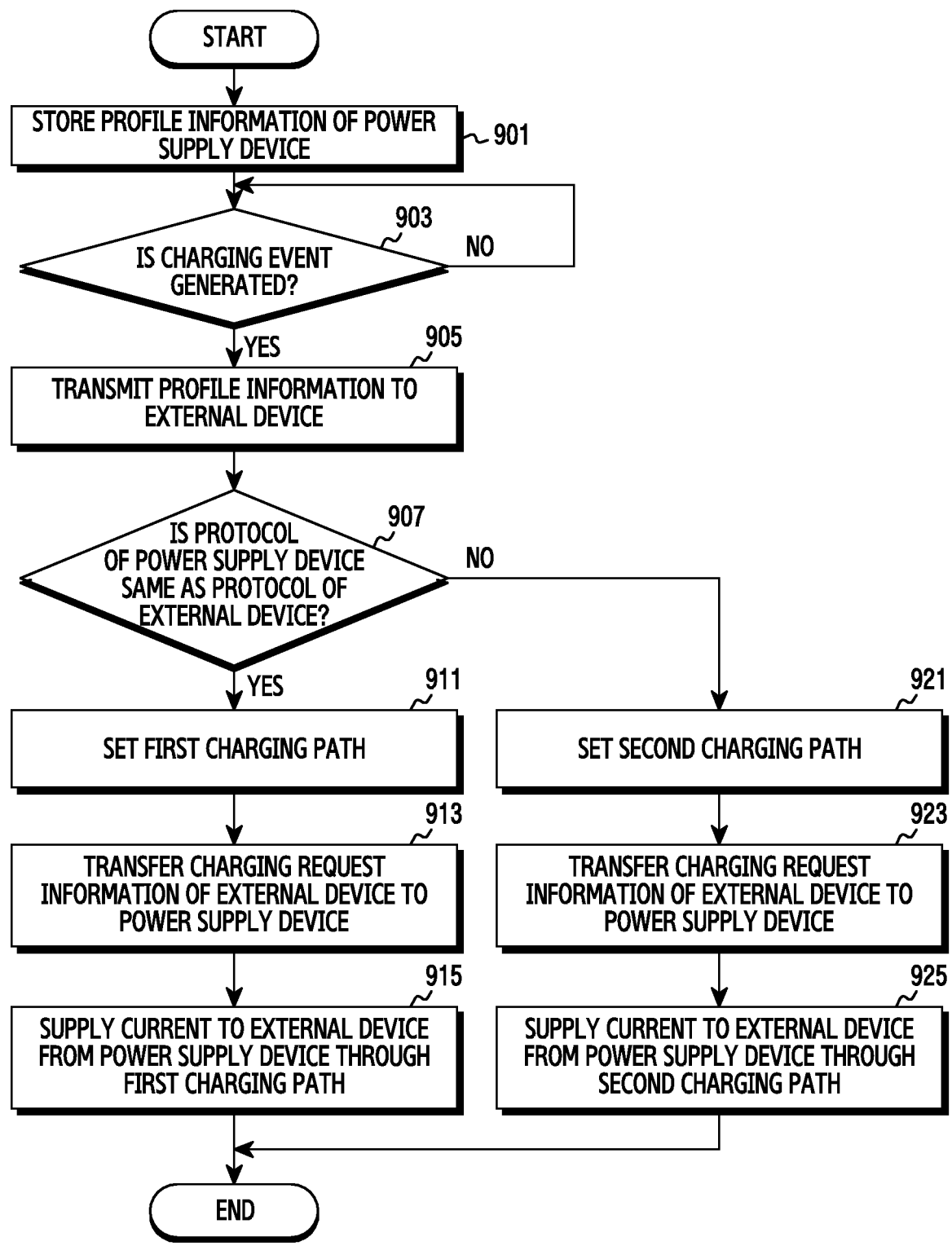
FIG. 9 is a flowchart illustrating a method of charging an external device by the electronic device according to various embodiments.

FIG. 9 is a flowchart illustrating a method of charging an external device by the electronic device according to various embodiments.

Referring to FIG. 9, in operation 901, the electronic device 420 (e.g., the control circuit 423) may store profile information of the power supply device 430. According to various embodiments, the electronic device 420 may be fixed to a predetermined location like a docking device and receive power from the power supply device 430. Accordingly, the power supply device 430 and the electronic device 420 may be connected. For example, the power supply device 430 is attachable to/detachable from the electronic device 420. FIG. 9 may illustrate an example of a case where the electronic device 420 is a docking device. Alternatively, FIG. 9 may illustrate a more detailed example of the operation of FIGS. 7 and 8.

In operation 903, the control circuit 423 of the electronic device 420 may determine whether a charging event is generated. The charging event may be an event connecting the external device 410 to the electronic device 420. For example, when the connection of the device is detected, the control circuit 423 may identify a connector connected to the device to check an identification or a capability of the connected device. When a signal is detected through at least one of the VBUS line, the CC1 line, and the CC2 line of the connector (e.g., the first connector 421), the control circuit 423 may detect that the external device 410 is connected to the first connector 421.

In operation 905, the control circuit 423 of the electronic device 420 may transmit the profile information to the external device 410. When the external device 410 is connected to the electronic device 420, the external device 410 may make a request for the profile. The control circuit 423 may transmit the stored profile information to the external device 410 in response to the profile request. For example, the control circuit 423 may transmit the stored profile information to the external device 410 through the CC1 line or the CC2 line of the first connector 421. For example, when the CC1 line of the first connector 421 is used as a communication path for making a request for the profile and receiving information, the CC2 line of the first connector 421 may be used as a power supply line (e.g., VCONN). Alternatively, when the CC2 line of the first connector 421 is used as a communication path for making a request for the profile and receiving information, the CC1 line of the first connector 421 may be used as a power supply line (e.g., VCONN).

The external device 410 may determine the voltage or the current to be charged based on the profile information. The external device 410 may transmit charging request information including the voltage or the current to be charged to the electronic device 420.

In operation 907, the control circuit 423 of the electronic device 420 may determine whether the protocol of the power supply device 430 is the same as the protocol of the external device 410. For example, the protocol of the external device 410 may be the same as the protocol of the power supply device 430, which is the protocol (e.g., USB 3.1 protocol) of the PD charging scheme. The USB 3.1 protocol may refer to communication through the CC1 line or the CC2 line. In another example, the protocol of the external device 410 may be the USB 3.1 protocol, and the protocol of the power supply device 430 may be the USB 2.0 protocol, which are different from each other. The USB 2.0 protocol may refer to communication through the D+ line and D- line. The control circuit 423 of the electronic device 420 according to an embodiment may perform operation 911 when the protocol of the power supply device 430 is the same as the protocol of the external device 410, and perform operation 921 when the protocol of the power supply device 430 is different from the protocol of the external device 410.

When the protocol of the power supply device 430 is the same as the protocol of the external device 410, the control circuit 423 may set a first charging path between the power supply device 430 and the external device 410 in operation 911. For example, when the protocol of the power supply device 430 and the protocol of the external device 410 correspond to the PD charging scheme, the control circuit 423 may set the first charging path to connect the CC1 line or the CC2 line of the first connector 421 and the CC line or the CC2 line of the second connector 425.

In operation 913, the control circuit 423 may transfer charging request information of the external device 410 to the power supply device 430 through the first charging path. The control circuit 423 may transfer the charging request information to the power supply device 430 through the CC1 line or the CC2 line of the second connector 425. For example, when the CC1 line of the first connector 421 is used as a communication path for making a request for the profile and receiving information, the CC2 line of the first connector 421 may be used as a power supply line (e.g., VCONN). Alternatively, when the CC2 line of the first connector 421 is used as a communication path for making a request for the profile and receiving information, the CC1 line of the first connector 421 may be used as a power supply line (e.g., VCONN). For example, the charging request information may correspond to a request for supplying the current of 9 V/1.6 A. In this case, the power supply device 430 may supply the current of 9 V/1.6 A.

In operation 915, the control circuit 423 may supply the current to the external device 410 from the power supply device 430 through the first charging path. The control circuit 423 may provide the current provided from the power supply device 430 to the external device 410. For example, while the power supply device 430 supplies 5 V/500 mA in operations 901 to 913, the power supply device 430 may boost the voltage to 9 V/1.6 A and supply the boosted voltage in operation 915. The external device 410 may receive the current provided from the power supply device 430 and drive the device or charge the battery.

When the protocol of the power supply device 430 is different from the protocol of the external device 410, the control circuit 423 may set a second charging path between the power supply device 430 and the external device 410 in operation 921. For example, the second charging path means that the electrically conductive path is formed between the CC1 line or the CC2 line of the first connector 421 and the D+ line and D- line of the second connector 425.

In operation 923, the control circuit 423 may transfer charging request information of the external device 410 to the power supply device 430 through the second charging path. For example, the control circuit 423 may transfer the charging request information to the power supply device 430 through the second charging path between the CC1 line or the CC2 line of the first connector 421 and the D+ line and D- line of the second connector 425. For example, the charging request information may correspond to a request for supplying the current of 9 V/1.6 A. In this case, the power supply device 430 may supply the current of 9 V/1.6 A.

In operation 925, the control circuit 423 may supply the current to the external device 410 from the power supply device 430 through the second charging path. The control circuit 423 may provide the current provided from the power supply device 430 to the external device 410. For example, while the power supply device 430 supplies 5 V/500 mA in operations 901 to 923, the power supply device 430 may boost the voltage to 9 V/1.6 A and supply the boosted voltage in operation 915. The external device 410 may receive the current provided from the power supply device 430 and drive the device or charge the battery.

For example, when the CC1 line of the first connector 421 is used as a communication path, the CC2 line of the first connector 421 may be used as a power supply line (e.g., VCONN). Alternatively, when the CC2 line of the first connector 421 is used as a communication path, the CC1 line of the first connector 421 may be used as a power supply line (e.g., VCONN). Further, the power supply is possible through the VBUS line. That is, the electrically conductive path may be formed between the VBUS line of the first connector 421 and the VBUS line of the second connector 425, and the power supply device 430 may provide the current to the external device 410 through the electrically conductive path.

Figure 10:
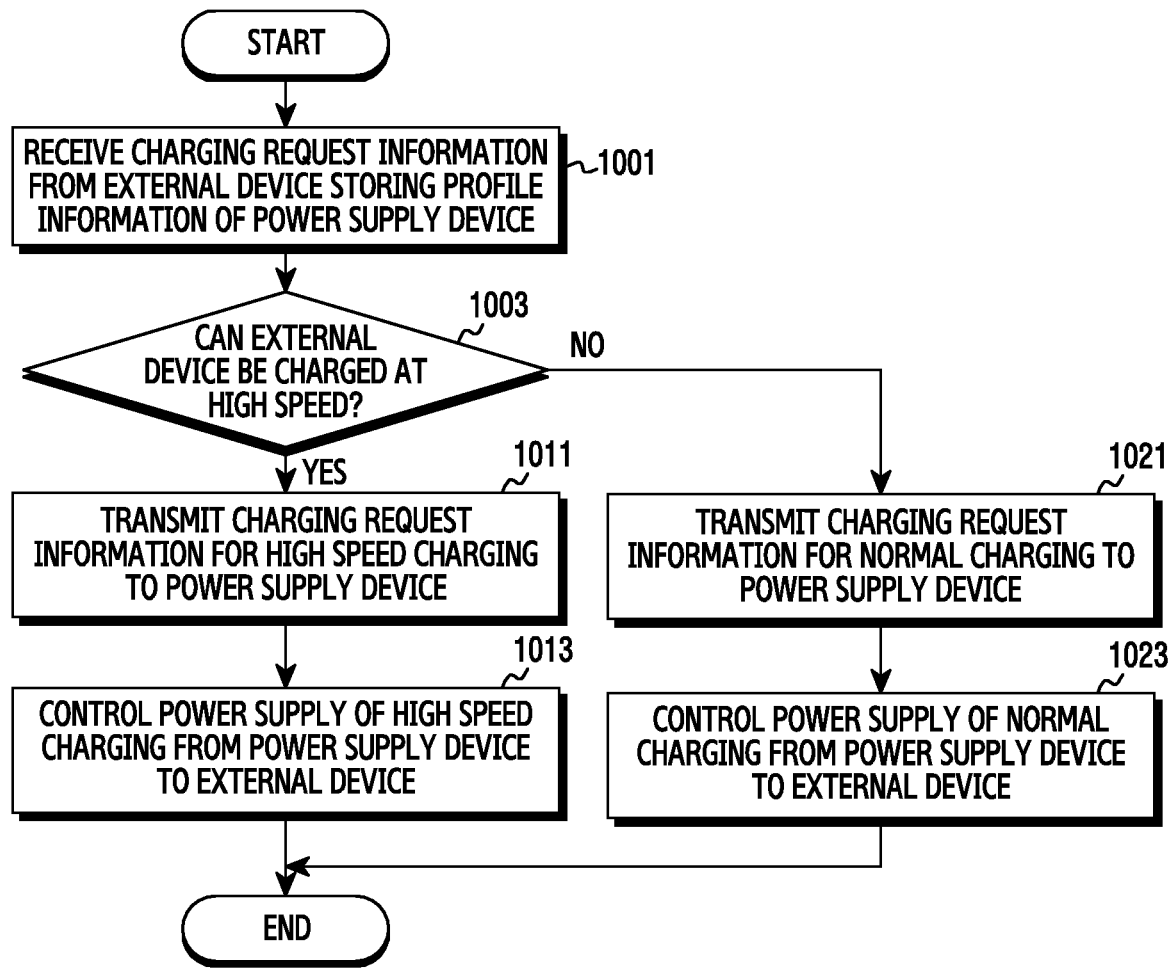
FIG. 10 is another flowchart illustrating the method of charging the external device by the electronic device according to various embodiments.

FIG. 10 is a flowchart illustrating a method of charging an external device by the electronic device according to various embodiments.

Referring to FIG. 10, in operation 1001, the electronic device 420 (e.g., the control circuit 423) may store profile information of the power supply device 430. Operation 1001 may refer to a state in which operations 701 to 709 of FIG. 7 have been performed or a state in which operations 901 and 907 of FIG. 9 have been performed. That is, the electronic device 420 may have completely made the connection with the power supply device 430 and the external device 410. The control circuit 423 may transmit the profile information to the external device 410 and receive charging request information from the external device 410.

In operation 1003, the control circuit 423 may determine whether the external device 410 can be charged at high speed. The control circuit 423 may determine whether the external device 410 can be charged at high speed based on the charging request information. For example, the control circuit 423 may determine whether the charging voltage (or current) included in the charging request information corresponds to the voltage for the high speed charging. Alternatively, the control circuit 423 may receive, from the external device 410, information on whether the high speed charging is supported. When the voltage for the high speed charging is 9 V or higher, the control circuit 423 may determine that the external device 410 can be charged at high speed if the charging voltage of the external device 410 is 9 V or higher and determine that the external device 410 cannot be charged at high speed if the charging voltage of the external device 410 is 9 V or lower.

The control circuit 423 may perform operation 1011 when the high speed charging is possible and perform operation 1021 when the high speed charging is impossible.

In operation 1011, the control circuit 423 may transmit charging request information for the high speed charging to the power supply device 430. For example, the power supply device 430 can perform both the high speed charging and the normal charging. Accordingly, voltages which can be provided by the power supply device 430 may include various voltages such as 5V, 9V, 12V, and 20V. For example, when the power supply device 430 provides the voltage of 5 V, the control circuit 423 may boost the voltage to 9 V in operation 1001.

In operation 1013, the control circuit 423 may control power supply of the high speed charging from the power supply device 430 to the external device 410. For example, the control circuit 423 may transfer power with the voltage of 9 V supplied from the power supply device 430 to the external device 410. At this time, when the protocol of the external device 410 is the same as the protocol of the power supply device 430, the control circuit 423 may provide the power supplied from the power supply device 430 to external device 410 through the first charging path. Alternatively, when the protocol of the power supply device 430 is different from the protocol of the external device 410, the control circuit 423 may provide the power supplied from the power supply device 430 to the external device 410 through the second charging path.

In operation 1021, the control circuit 423 may transmit charging request information for the normal charging to the power supply device 430. For example, the power supply device 430 can perform both the high speed charging and the normal charging. Accordingly, the voltages which can be provided by the power supply device 430 may include various voltages such as 3 V, 5 V, 9 V, 12 V, and 20 V. When the charging request information received from the external device 410 corresponds to the normal charging voltage, the electronic device 420 according to an embodiment may determine that the external device 410 does not support the high speed charging.

According to an embodiment, the external device 410 may make a request for the voltage for the normal charging based on environment information (e.g., temperature or operational state) of the external device 410 although the external device 410 supports the high speed charging. For example, when the power supply device 430 provides the voltage of 3 V, the control circuit 423 may boost the voltage to 5 V in operation 1001. Alternatively, when the power supply device 430 provides the voltage of 5 V, the control circuit 423 may maintain the voltage as 5 V in operation 1001.

In operation 1023, the control circuit 423 may control power supply of the normal charging from the power supply device 430 to the external device 410. For example, the control circuit 423 may transfer power with the voltage of 5 V supplied from the power supply device 430 to the external device 410. In the normal charging, the power supply device 430 may supply the current to the external device 410 through the VBUS line.

According to various embodiments, when the protocol of the external device 410 is the same as the protocol of the power supply device 430, the control circuit 423 may provide the power supplied from the power supply device 430 to external device 410 through the first charging path. Alternatively, when the protocol of the power supply device 430 is different from the protocol of the external device 410, the control circuit 423 may provide the power supplied from the power supply device 430 to the external device 410 through the second charging path.

Figure 11:
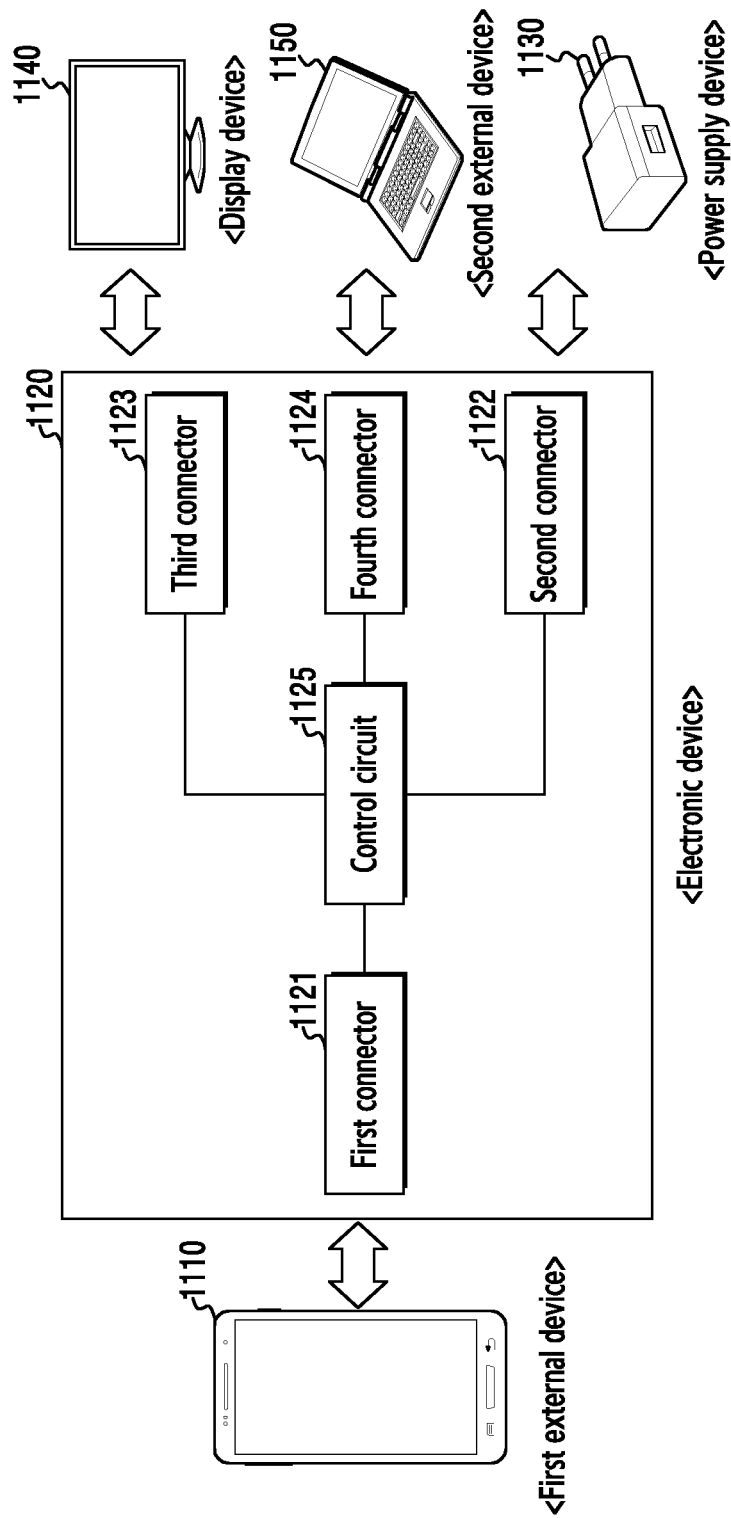
FIG. 11 illustrates a connection relationship between the electronic device and external devices according to various embodiments.

FIG. 11 illustrates a connection relationship between the electronic device and external devices according to various embodiments.

Referring to FIG. 11, an electronic device 1120 may be connected to a first external device 1110, a power supply device 1130, a display device 1140, and a second external device 1150.

The first external device 1110 according to an embodiment of the present disclosure may be the electronic device 101 illustrated in FIG. 1 or the electronic device 201 illustrated in FIG. 2. When the first external device 1110 is connected to the electronic device 1120, the first external device 1110 may receive power from the power supply device 1130. That is, the first external device 1110 may be equal or similar to the external device 410 of FIG. 4.

The electronic device 1120 according to an embodiment of the present disclosure may include a first connector 1121 (or a first electrical interface), a second connector 1122 (or a second electrical interface), a third connector 1123 (or a third electrical interface), a fourth connector 1124 (or a fourth electrical interface), and a control circuit 1125.

A USB type C interface may be adopted as the first connector 1121. The USB type C interface supports a USB 3.1 protocol and the USB 3.1 protocol corresponds to a protocol which can provide a maximum of 100 W power with a maximum of 20 V and 5 A. The first connector 1121 may be electrically connected to the first external device 1110. When the first external device 1110 is connected, the first connector 1121 may detect a signal in at least one of a VBUS pin, a CC1 pin, and a CC2 pin.

The second connector 1122 may be electrically connected to the power supply device 1130. A type of interface that supports a USB 2.0 specification or higher may be adopted as the second connector 1122. For example, the type that supports the USB 2.0 specification or higher may include various types such as type B and type C. Further, a protocol supporting the USB 2.0 specification or higher may be at least one of a USB 2.0 protocol, a USB 3.0 protocol and a USB 3.1 protocol. The second connector 1122 may have a different number of conductive pins according to the USB specification or type.

A High Definition Multimedia Interface (HDMI) may be adopted as the third connector 1123. The third connector 1123 may be electrically connected to the display device 1140. A USB 2.0 type A interface may be adopted as the fourth connector 1124. The fourth connector 1124 may be connected to the second external device 1150. The control circuit 1125 is an MCU and may detect whether a device is connected to the first connector 1121 to the fourth connector 1124 and form a plurality of electrically conductive paths directly or indirectly connected between the first connector 1121 to the fourth connector 1124.

When the first external device 1110 is connected to the first connector 1121, the control circuit 1125 according to an embodiment of the present disclosure may provide power supplied from the power supply device 1130 connected to the second connector 1122 to the first external device 1110.

For example, when the charging scheme of the first external device 1110 is the same as the charging scheme of the power supply device 1130, the control circuit 1125 may provide power supplied from the power supply device 1130 to the first external device 1110 through a first charging path. When the charging scheme of the first external device 1110 is different from the charging scheme of the power supply device 1130, the control circuit 1125 may provide power supplied from the power supply device 1130 to the first external device 1110 through a second charging path.

The power supply device 1130 according to an embodiment of the present disclosure may be a charger, and may perform high speed charging or normal charging. The power supply device 1130 may provide power through various protocols. For example, the power supply device 1130 may supply power through one of the AFC, QC, and PD charging schemes. For example, the power supply device 1130 may be equal or similar to the power supply device 430 of FIG. 4.

The display device 1140 according to an embodiment of the present disclosure may be connected to the third connector 1123 and thus may display data transferred from the first external device 1110. For example, the display device 1140 may include a Liquid Crystal Display (LCD), a Light Emitting Diode (LED) display, an Organic Light Emitting Diode (OLED) display, a Micro Electro Mechanical System (MEMS) display, or an electronic paper display.

The second external device 1150 according to an embodiment of the present disclosure may be connected to the fourth connector 1124 and thus may perform data communication with the first external device 1110. The second external device 1150 may be the electronic device 101 illustrated in FIG. 1 or the electronic device 201 illustrated in FIG. 2. The second external device 1150 may include a terminal which can perform data communication with the first external device 1110. For example, the second external device 1150 may perform data communication with the first external device 1110 through D+/D− lines. The data communication through the D+/D− lines may be USB 2.0. Alternatively, the second external device 1150 may perform data communication with the first external device 1110 through TX/RX lines. The data communication through the RX/TX lines may be USB 3.1.

Figure 12A:
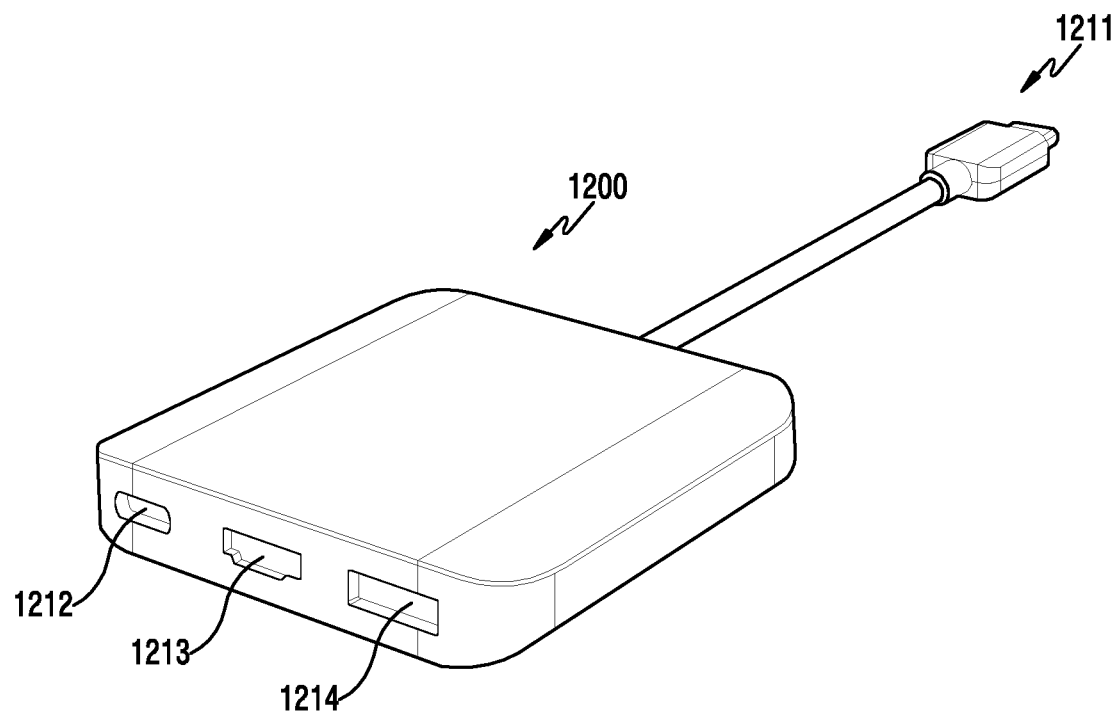
FIG. 12A and FIG. 12B are a perspective view and internal circuit diagram of the electronic device according to various embodiments.
Figure 12B:
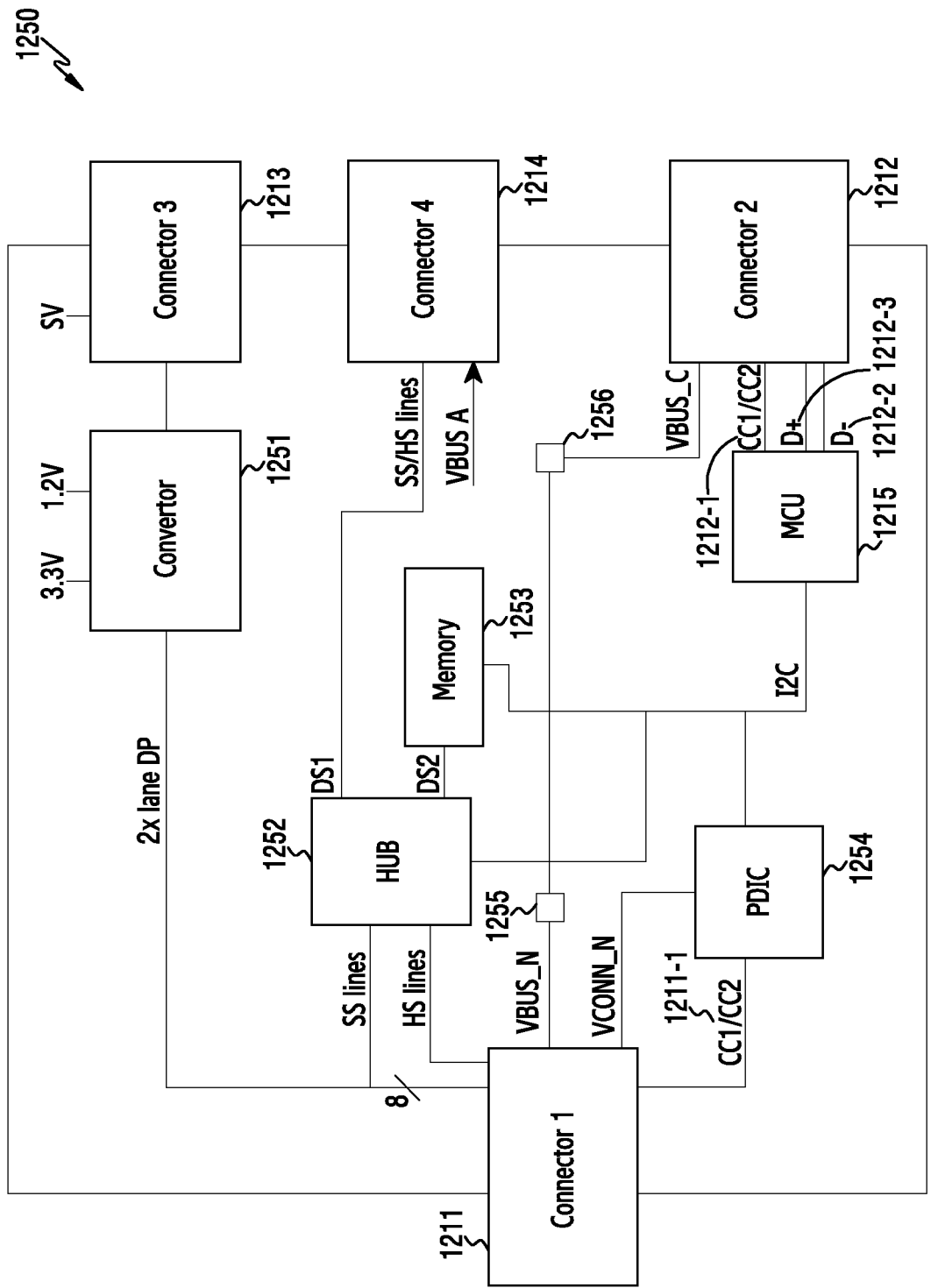

FIGS. 12A and 12B are a perspective view and an internal circuit diagram of the electronic device according to various embodiments.

FIG. 12A is a perspective view isometrically illustrating a portion of an electronic device 1200, where a second connector 1122, a third connector 1213 and a fourth connector 1124 of the electronic device 1200 (e.g., 1120 of FIG. 11) are formed.

Referring to FIG. 12A, an electronic device 1200 may include a housing (or body), a control circuit 1125 within the housing, a first connector 1211, a second connector 1212, a third connector 1213, and a fourth connector 1214. The first connector 1211 may be connected to the housing through a cable having a predetermined length. The first connector 1211 may be connected to the first external device 1110, the second connector 1212 may be connected to the power supply device 1130, the third connector 1213 may be connected to the display device 1140, and the fourth connector 1214 may be connected to the second external device 1150.

For example, the first connector 1211 may be a male connector, and the second connector 1212, the third connector 1213, and the fourth connector 1214 may be female connectors. Although the first connector 1211, the second connector 1212, the third connector 1213, and the fourth connector 1214 are illustrated in different forms (e.g., female connector and male connector) in the perspective view, the first connector 1211, the second connector 1212, the third connector 1213, and the fourth connector 1214 may be implemented in the same form (e.g., female connector/female connector or male connector/male connector) according to a design of the electronic device 1220 or the female connector and the male connector illustrated in the perspective view may be inversely implemented.

FIG. 12B is a schematic internal circuit diagram of the electronic device 1120.

Referring to FIG. 12B, the electronic device 1200 may include the first connector 1211, the second connector 1212, the third connector 1213, the fourth connector 1214, an MCU 1215, a converter 1251, a HUB 1252, a memory 1253, and a PDIC 1254.

The first connector 1211 according to an embodiment of the present disclosure may be a USB type C connector. For example, the first connector 1211 may include the first number of conductive pins arranged according to the first protocol. The second connector 1212 may include the second number of conductive pins arranged according to the second protocol different from the first protocol, the second number being different from the first number.

When the first external device 1110 is connected to the first connector 1211, the PDIC 1254 may detect a signal in a CC1/CC2 line 1211-1 or a VBUS line (VBUS_N). When the signal is detected, the PDIC 1254 may recognize that the first external device 1110 is connected and notify the MCU 1215 of the connection of the first external device 1110. When a signal is detected through the VBUS line (VBUS_N) or the CC1/CC2 line 1211-1, the PDIC 1254 may turn on a first switch 1255. When the CC1 line between the CC1/CC2 lines 1211-1 is used for a communication path, the CC2 line may be used as a terminal that receives power such as VCONN_N.

When the signal received from the PDIC 1254, the MCU 1215 may determine that charging scheme of the first external device 1110 is the PD. The MCU 1215 may receive a request for transmitting profile information from the first external device 1110 through the CC1/CC2 line 1211-1. When the power supply device 1130 is connected to the second connector 1212, the MCU 1215 may detect a signal in a VBUS line (VBUS_C) or a CC1/CC2 line 1212-1. When the signal is received in the CC1/CC2 line 1212-1, the MCU 1215 may determine that the charging scheme of the power supply device 1130 is the PD. The MCU 1215 may make a request for the profile information to the power supply device 1130 through the CC1/CC2 line 1212-1. The MCU 1215 may detect the signal through a VBUS line (VBUS_N) or a D+ line 1212-3 and a D− line 1212-2 of the second connector 1212. When it is determined that the power supply device 1130 is connected through the D+ line 1212-3 and the D− line 1212-2 of the second connector 1212, the MCU 1215 may determine that the charging scheme of the power supply device 1130 is the AFC or the QC. The MCU 1215 may make a request for the profile information to the power supply device 1130 through the D+ line 1212-3 and the D− line 1212-2. When a signal is detected through the VBUS line (VBUS_C) or the CC1/CC2 line 1212-1, the MCU 1215 may turn on a second switch 1256.

When the first switch 1255 is turned on and the second switch 1256 is turned on, the VBUS line (VBUS_N) of the first connector 1211 and the VBUS line (VBUS_C) of the second connector 1212 may be connected to each other. That is, as the VBUS line is connected between the first switch 1255 and the second switch 1256, the first external device 1110 may receive the current from the power supply device 1130 through the VBUS line.

Since the first connector 1211 and the second connector 1212 are equal or similar to the first connector 421 and the second connector 425 of FIG. 4, a detailed description will be omitted in FIG. 12B.

The third connector 1213 may include a third number of conductive pins arranged according to a third protocol different from the first connector 1211 or the second connector 1212, the third number of conductive pins being different from the second number of conductive pins which is different from the first number. For example, the third protocol may include at least one of a High Definition Multimedia Interface (HDMI) protocol and an Audio/Video (AV) protocol. The fourth connector 1214 may include a fourth number of conductive pins arranged according to a fourth protocol different from the first connector 1211 to the third connector 1213, the fourth number of conductive pins being different from the first number of the third number of conductive pins. For example, as the fourth protocol, a USB 2.0 type A interface may be adopted.

An SS line and an HS line of the first connector 1211 correspond to an RX/TX line and may form an electrically conductive path with an SS line and an HS line of the fourth connector 1214. The first external device 1110 connected to the first connector 1211 and the second external device connected to the fourth connector 1214 may perform data communication through the SS line and the HS line. The data communication through the RX/TX lines may be USB 3.1.

When the display device 1140 is connected to the third connector 1213 according to an embodiment of the present disclosure, the signal may be detected by the conductive pins included in the third connector 1213. When it is determined that the display device 1140 is connected to the third connector 1213, the MCU 1215 may transmit data to the display device 1140. At this time, the converter 1251 may convert data received from the first external device 1110 into Display Port (DP) to HDMI. For example, when a display standard of the first external device 1110 does not match a display standard of the display device 1140, the converter 1251 may convert data received from the first external device 1110 to match the display standard of the display device 1140. The converter 1251 may convert data received from the first external device 1110 to match the display standard of the display device 1140. The converted data may be provided to the display device 1140 through the third connector 1213.

When many external devices are connected to the electronic device 1250, the HUB 1252 may control data communication between the external devices according to a control of the MCU 1215. For example, when the display device 1140 is connected to the third connector 1213 and the second external device 1150 is connected to the fourth connector 1214, the HUB 1252 may provide video data output from the first external device 1110 to the display device 1140 and data output from the first external device 1110 to the second external device 1150. Further, the HUB 1252 may provide data output from the second external device 1150 to the first external device 1110.

The memory 1253 may store information on a device connected to each connector. For example, the memory 1253 may store at least one piece of information on the first external device 1110 connected to the first connector 1211, information on the power supply device 1130 connected to the second connector 1212, information on the display device 1140 connected to the third connector 1213, and information on the second external device 1150 connected to the fourth connector 1214. For example, the information on the display device 1140 may include at least one of an identifier of the display device 1140, a protocol, a driving voltage, a display size, a resolution, and a transmission speed. For example, the information on the second external device 1150 may include an identifier of the second external device 1150, a protocol, a storage capacity, a data processing speed, data throughput, a transmission speed, a driving voltage, a display size, and a resolution.

The MCU 1215 according to an embodiment of the present disclosure may provide power supplied from the power supply device 1130 to the first external device 1110 through the VBUS line (VBUS_C) or the CC1/CC2 line 1212-1. The MCU 1215 according to an embodiment of the present disclosure may determine whether the charging scheme of the first external device 1110 is the same as the charging scheme of the power supply device 1130. For example, when the charging scheme (e.g., PD) of the first external device 1110 is the same as the charging scheme (e.g., PD) of the power supply device 1130, the MCU 1215 may provide power supplied from the power supply device 1130 to the first external device 1110 through a first charging path. When the charging scheme (e.g., PD) of the first external device 1110 is different from the charging scheme (e.g., AFC or QC) of the power supply device 1130, the MCU 1215 may provide power supplied from the power supply device 1130 to the first external device 1110 through a second charging path.

Figure 13:
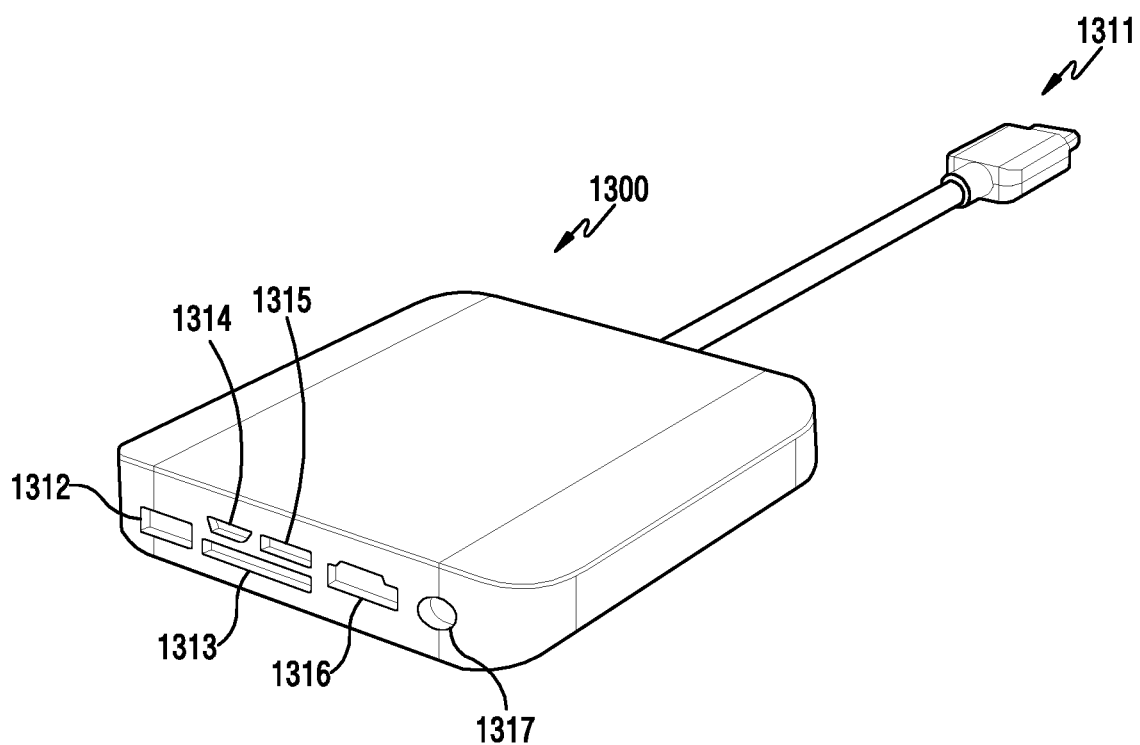
FIG. 13 is an external configuration diagram of the electronic device according to various embodiments.

FIG. 13 is a perspective view illustrating the electronic device according to various embodiments.

Referring to FIG. 13, an electronic device 1300 may include a housing (or body), a control circuit 1125 within the housing (e.g., from FIG. 11), a first connector 1311, a second connector 1312, a third connector 1316, a fourth connector 1317, a first memory card insertion unit 1313, a second memory card insertion unit 1314, and a third memory card insertion unit 1315. The first connector 1311 may be connected to the housing through a cable having a predetermined length. The first connector 1311 may be connected to the first external device 1110, the second connector 1312 may be connected to the power supply device 1130, the third connector 1316 may be connected to the display device 1140, and the fourth connector 1317 may be connected to a speaker.

For example, the first connector 1311 may be a male connector, and the second connector 1312, the third connector 1316, and the fourth connector 1317 may be female connectors. Although the first connector 1311, the second connector 1312, the third connector 1316, and the fourth connector 1317 are illustrated in different forms (e.g., female connector and male connector) in the perspective view, the first connector 1311, the second connector 1312, the third connector 1316, and the fourth connector 1317 may be implemented in the same form (e.g., female connector/female connector or male connector/male connector) according to a design of the electronic device 1300 or the female connector and the male connector illustrated in the perspective view may be inversely implemented.

For example, the first connector 1311 may be a USB 3.1 type C connector, and the second connector 1312 may be USB 2.0 type A connector. The third connector 1316 may be an HDMI terminal. The fourth connector 1317 may be an Audio/Video (AV) output terminal. The first memory card insertion unit 1313 may be an Secure Digital (SD) memory card insertion terminal. The first memory card insertion unit 1313 may include a fifth number of conductive pins which can recognize the SD memory card. The control circuit 1125 may read data stored in the SD memory card by using at least one of the fifth number of conductive pins. The second memory card insertion unit 1314 may be a micro USB insertion terminal. The third memory card insertion unit 1315 may be a micro SD card insertion terminal.

The electronic device 1300 according to an embodiment of the present disclosure may be implemented to include various forms of connectors as illustrated in FIGS. 5A, 12A, and 13. For example, at least one of the various forms of connectors (e.g., USB 2.0 type A connector, HDMI terminal, AV output terminal, and memory card recognition terminal) illustrated in FIG. 13 may be included in the electronic device illustrated in FIG. 5A.

A method of operating an electronic device may include an operation of making a connection with an external device by using at least one of a first number of conductive pins arranged according to a first protocol of a first connector; an operation of receiving profile information indicating a capability of a power supply device connected through at least one of a second number of conductive pins arranged according to a second protocol of a second connector different from the first connector or an identification of an external device; and an operation of setting a charging path between the first connector and the second connector by using the conductive pin connected to the external device and the conductive pin connected to the power supply device.

The conductive pin connected to the external device may be a CC1 pin or a CC2 pin, and the conductive pin connected to the power supply device may include one of the CC1 pin and the CC2 pin, a D+ pin, and a D− pin.

When the conductive pin connected to the external device and the conductive pin connected to the power supply device correspond to the CC1 pin or the CC2 pin, the operation of setting the charging path may include an operation of setting a first charging path to form an electrically conductive path between the CC1 pin or the CC2 pin of the first connector and the CC1 pin or the CC2 pin of the second connector.

When the conductive pin connected to the external device is the CC1 pin or the CC2 pin and the conductive pin connected to the power supply device is the D+ pin and the D− pin, the operation of setting the charging path may include an operation of setting a second charging path to form an electrically conductive path between the CC1 pin or the CC2 pin of the first connector and the D+ pin and the D− pin of the second connector.

When the conductive pin connected to the power supply device is the CC1 pin or the CC2 pin, the method may further include an operation of determining that a charging scheme of the power supply device corresponds to Power Delivery (PD).

When the conductive pin connected to the power supply device is the D+ pin and the D− pin, the method may further include an operation of determining that a charging scheme of the power supply device corresponds to Adaptive Fast Charging (AFC) or Quick Charge (QC).

The profile information may be configured to allow provision of voltages at multiple levels for charging.

The method may further include an operation of providing a signal transmitted from the external device through a third connector including a third number of conductive pins arranged according to a third protocol different from the first protocol and the second protocol, the third number being different from the first number and the second number.

The method may further include an operation of passing a signal transmitted from the external device to a fourth connector including a fourth number of conductive pins arranged according to a fourth protocol.

The computer readable recoding medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), and the like. In addition, the program instructions may include high class language codes, which can be executed in a computer by using an interpreter, as well as machine codes made by a compiler. The aforementioned hardware device may be configured to operate as one or more software modules in order to perform the operation of the present disclosure, and vice versa.

Any of the modules or programming modules according to various embodiments of the present disclosure may include at least one of the above described elements, exclude some of the elements, or further include other additional elements. The operations performed by the modules, programming module, or other elements according to various embodiments of the present disclosure may be executed in a sequential, parallel, repetitive, or heuristic manner. Further, some operations may be executed according to another order or may be omitted, or other operations may be added. Various embodiments disclosed herein are provided merely to easily describe technical details of the present disclosure and to help the understanding of the present disclosure, and are not intended to limit the present disclosure. Therefore, it should be construed that all modifications and changes or modified and changed forms based on the technical idea of the present disclosure fall within the present disclosure.

The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

The control unit may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc.

In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for". In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

What is claimed is:

1. An electronic device comprising:
a first connector including first conductive pins arranged according to a first protocol;
a second connector including second conductive pins arranged according to a second protocol different from the first protocol, the second conductive pins being different in number from the first conductive pins; and
a control circuit operatively coupled to the first connector and the second connector, wherein the control circuit is configured to:
detect coupling to an external device through the first connector by at least one of the first conductive pins,
receive profile information including at least one of: a power supply device operatively coupled to the second connector by at least one of the second conductive pins, and identification information for an external device, and
set a charging path within the electronic device between the first connector and the second connector using at least one of the first conductive pins and the at least one of the second conductive pins coupled to the power supply device,
wherein the at least one of the first conductive pins operatively coupled to the external device is a Configuration Channel 1 (CC1) pin or a Configuration Channel 2 (CC2) pin, and at least one of the second conductive pins operatively coupled to the power supply device includes at least one of a second CC1 pin, a second CC2 pin, a D+ pin, and a D– pin, and
wherein when the first conductive pin operatively coupled to the external device and the second conductive pin operatively coupled to the power supply device correspond to the CC1 pin, the CC2 pin, the second CC1 pin and the second CC2 pin, the control circuit is configured to set a first charging path including an electrically conductive path between the CC1 pin or the CC2 pin of the first connector and the second CC1 pin or the second CC2 pin of the second connector.

2. The electronic device of claim 1, wherein:
when the first conductive pin operatively coupled to the external device is the CC1 pin or the CC2 pin and the second conductive pin operatively coupled to the power supply device is the D+ pin and the D– pin, the control circuit is configured to set a second charging path including an electrically conductive path between the CC1 pin or the CC2 pin of the first connector and the D+ pin or the D– pin of the second connector.

3. The electronic device of claim 1, wherein:
when the second conductive pin operatively coupled to the power supply device is the CC1 pin or the CC2 pin, the control circuit is configured to detect a charging scheme of the power supply device to be a "Power Delivery" (PD) specification.

4. The electronic device of claim 1, wherein:
when the second conductive pin operatively coupled to the power supply device is the D+ pin and the D– pin, the control circuit is configured to detect a charging scheme of the power supply device to be "Adaptive Fast Charging" (AFC) specification or "Quick Charge" (QC) specification.

5. The electronic device of claim 1, wherein the received profile information includes information implementing a plurality of voltages for multiple levels of charging.

6. The electronic device of claim 1, further comprising a third connector including third conductive pins arranged according to a third protocol different from the first protocol and the second protocol, the third conductive pins having a number from the first conductive pins and the second conductive pins,
wherein the control circuit is operatively coupled to the third connector and configured to provide a signal transmitted from the external device through at least one of the third conductive pins.

7. The electronic device of claim 6, wherein the third connector includes at least one of a USB 2.0 type A connector, a High Definition Multimedia Interface (HDMI) terminal, Audio/Video (A/V) output terminal, and a memory card recognition terminal.

8. The electronic device of claim 1, further comprising a fourth connector including fourth conductive pins arranged according to a fourth protocol,
wherein the control circuit is electrically coupled to the fourth connector and configured to forward a signal received from the external device to the fourth connector.

9. The electronic device of claim 8, wherein the control circuit is configured to set an electrically conductive path for data communication between the first connector and the fourth connector.

10. A method in an electronic device, comprising:
detecting an operative coupling of an external device with the electronic device using at least one of first conductive pins arranged according to a first protocol of a first connector;
receiving at least one of:
profile information indicating a capability of a power supply device operatively coupled through at least one of second conductive pins arranged according to a second protocol of a second connector different from the first protocol, the second conductive pins being different in number from the first conductive pins, and
identification for the external device; and
setting a charging path between the first connector and the second connector using at least one of the first conductive pins operatively coupled to the external device and the at least one of the second conductive pins operatively coupled to the power supply device,
wherein the first conductive pins operatively coupled to the external device include a Configuration Channel 1 (CC1) pin or a Configuration Channel (CC2) pin, and the second conductive pin operatively coupled to the power supply device include one of a second CC1 pin, a second CC2 pin, a D+ pin, and a D– pin, and
wherein setting the charging path further comprises:
when the first conductive pins operatively coupled to the external device and the second conductive pins operatively coupled to the power supply device correspond to the CC1 pin, the second CC1 pin, the CC2 pin or the second CC2 pin, a first charging path is set including an electrically conductive path between the CC1 pin or the CC2 pin of the first connector and the second CC1 pin or the second CC2 pin of the second connector.

11. The method of claim 10, wherein setting the charging path comprises:
when the first conductive pins operatively coupled to the external device includes the CC1 pin or the CC2 pin and the second conductive pins operatively coupled to the power supply device include the D+ pin and the D− pin, a second charging path is set including an electrically conductive path between the CC1 pin or the CC2 pin of the first connector and the D+ pin and the D− pin of the second connector.

12. The method of claim 10, further comprising:
when the first conductive pins operatively coupled to the power supply device includes the CC1 pin or the CC2 pin, detecting that a charging scheme of the power supply device corresponds to a "Power Delivery" (PD) specification.

13. The method of claim 10, further comprising:
when the second conductive pins operatively coupled to the power supply device is the D+ pin and the D− pin, detecting that a charging scheme of the power supply device corresponds to an "Adaptive Fast Charging" (AFC) specification or "Quick Charge" (QC) specification.

14. The method of claim 10, wherein the received profile information includes information implementing a plurality of voltages for multiple levels of charging.

15. The method of claim 10, further comprising:
providing a signal transmitted from the external device through a third connector including third conductive pins arranged according to a third protocol different from the first protocol and the second protocol, the third conductive pins being different in number from the first conductive pins and the second conductive pins.

16. The method of claim 10, further comprising:
forwarding a signal received from the external device to a fourth connector including fourth conductive pins arranged according to a fourth protocol.

* * * * *